US008779002B2

(12) United States Patent
Schubert

(10) Patent No.: US 8,779,002 B2
(45) Date of Patent: Jul. 15, 2014

(54) METHODS FOR TREATING A VARIETY OF DISEASES AND CONDITIONS, AND COMPOUNDS USEFUL THEREFOR

(75) Inventor: David R. Schubert, La Jolla, CA (US)

(73) Assignee: Salk Institute for Biological Studies, LaJolla, CA (US)

( * ) Notice: Subject to any disclaimer, the term of this patent is extended or adjusted under 35 U.S.C. 154(b) by 396 days.

(21) Appl. No.: 12/682,767

(22) PCT Filed: Oct. 14, 2008

(86) PCT No.: PCT/US2008/079874
§ 371 (c)(1),
(2), (4) Date: Jul. 1, 2010

(87) PCT Pub. No.: WO2009/052116
PCT Pub. Date: Apr. 23, 2009

(65) Prior Publication Data
US 2010/0305181 A1     Dec. 2, 2010

Related U.S. Application Data

(60) Provisional application No. 60/980,109, filed on Oct. 15, 2007.

(51) Int. Cl.
*A61K 31/136* (2006.01)
*C07C 243/18* (2006.01)

(52) U.S. Cl.
CPC ................................. *A61K 31/136* (2013.01); *C07C 243/18* (2013.01)
USPC .......................................... 514/614; 564/151

(58) Field of Classification Search
CPC ............................ A61K 31/136; C07C 243/18
USPC .......................................... 514/614; 564/151
See application file for complete search history.

(56) References Cited

U.S. PATENT DOCUMENTS

| | | | |
|---|---|---|---|
| 6,313,150 B1 | 11/2001 | Ohtsuka et al. | |
| 6,362,212 B1 | 3/2002 | Takase et al. | |
| 2006/0276433 A1 * | 12/2006 | Kawagoe et al. | 514/63 |
| 2007/0238700 A1 | 10/2007 | Winzenberg et al. | |
| 2012/0282629 A1 | 11/2012 | Wanker et al. | |

FOREIGN PATENT DOCUMENTS

| | | |
|---|---|---|
| EP | 0160408 A1 | 11/1985 |
| EP | 1612204 A1 | 1/2006 |
| GB | 744686 A | 2/1956 |
| JP | 54-136821 A | 10/1979 |
| WO | WO 98/47869 A1 | 10/1998 |
| WO | WO 2007/043401 A1 | 4/2007 |
| WO | WO 2013/104631 | 7/2013 |

OTHER PUBLICATIONS

Goel, Anshu. Structure-Activity Study on Anti-inflammatory Pyrazole Carboxylic Acid Hydrazide Analogs Using Molecular Connectivity Indices. J. Chem. Inf. Comput. Sci. 1995, 35, 510-514.*
Aubin, S. et al.; "Retro hydrazine-azapeptoids as peptidomimetics of proteasome inhibitors"; 2005, *Journal of Medicinal Chemistry*, vol. 48, No. 1, pp. 330-334.
Kenyon, W. et al.; "Alkylations of Ketone and ALdehyde Phenylhydrazones by means of Alkali Amides in Liquid Ammonia to form N-alkyl Derivatives"; 1965, *Journal of Organic Chemistry*, vol. 30, pp. 292-293.
Madsen, P. et al.; "N, N-Dibenzyl-N'-benzylidenehydrazines: Potent Competitive Glucose-6-phosphate Catalytic Enzyme Inhibitors"; 2001, *Bioorganic & Medicinal Chemistry Letters*, vol. 11, pp. 2165-2167.
Ono, T. et al.; "Optodynamers: expression of color and fluorescence at the interface between two films of different dynamic polymers"; 2007, *Chemical Communication*, pp. 4360-4362.

* cited by examiner

*Primary Examiner* — Samantha Shterengarts
(74) *Attorney, Agent, or Firm* — Klarquist Sparkman LLP

(57) ABSTRACT

In accordance with the present invention, there are provided novel compounds that have a variety of properties, i.e., antioxidant, anti-inflammatory, antiviral, antibacterial, and antifungal properties. Invention compounds, therefore, have the ability to impart a variety of beneficial physiological effects, e.g., to protect neurons and/or to promote neuroregeneration and/or to promote memory formation and/or to act as protein phosphatase or kinase inhibitors and/or to act as lipoxygenase inhibitors. Such compounds are useful for treatment of a variety of indications, including neurodegenerative diseases and conditions, diabetes, ischemia associated with heart disease, and memory deficit. In another aspect of the present invention, there are also provided formulations containing one or more of the above-described compounds, optionally further containing additional neurologically active compound(s) and/or adjuvants to facilitate delivery thereof across the blood/brain barrier. In still another aspect of the present invention, there are further provided methods for treating a wide variety of neurological indications, e.g., acute neural injuries, chronic injuries, promoting memory formation, and the like.

12 Claims, 6 Drawing Sheets

METHODS FOR TREATING A VARIETY OF DISEASES AND CONDITIONS, AND COMPOUNDS USEFUL THEREFOR

GOVERNMENT ACKNOWLEDGEMENT

This invention was made with United States government support under Grant Nos. NS-10279, NS-09658 and NS-28121 from the National Institutes of Health. The United States Government has certain rights in this invention.

FIELD OF THE INVENTION

The present invention relates to novel compounds which are useful for the treatment of a variety of indications, including neurodegenerative diseases and conditions, diabetes, ischemia associated with heart disease, and memory deficit, as well as for protection against such indications, e.g., neurodegenerative diseases and conditions, diabetes, ischemia associated with heart disease, and memory deficit. In a particular aspect, the present invention relates to methods for the treatment of neurodegenerative diseases and conditions, diabetes, ischemia associated with heart disease, and memory deficit employing invention compounds. In a further aspect, the present invention relates to methods for protecting neurons in a subject in need thereof. In still another aspect, the present invention relates to methods for promoting neuroregeneration in a subject in need thereof. In yet another aspect, the present invention relates to methods for promoting memory formation in a subject in need thereof.

BACKGROUND OF THE INVENTION

There are currently few if any effective drug treatments for acute neural injuries (such as stroke and spinal cord injury) and chronic neurodegenerative diseases (such as Alzheimer's disease, Parkinson's disease, Huntington's disease, amytrophical lateral sclerosis, retinal degeneration, etc.). Accordingly, drugs that can protect neurons and/or promote neuroregeneration are urgently needed to treat these devastating injuries or diseases, as well as promote memory formation. Additional targets of interest include CaM Kinase II, which is involved in memory formation, and tyrosine phosphatase, which involved in such diseases as diabetes.

Neurotrophic growth factors (including e.g., nerve growth factor, brain-derived neurotrophic factor, neurotrophin-3, neurotrophin-4/5, ciliary neurotrophic factor, glial cell-derived neurotrophic factor, fibroblast growth factor and the like) have emerged in the past decade as promising drug candidates for treating acute and chronic neurodegenerative diseases. These protein neurotrophic growth factors play an essential role in the maintenance of neuronal populations from development through adulthood. However, clinical studies with these protein-based neurotrophic factors have proved to be disappointing due to their poor pharmacokinetic behavior, low bioavailability, inability to penetrate the brain, and pleiotropic effects. Therefore, much effort has been invested in the search for non-peptidyl small neurotrophic molecules.

Small neurotrophic molecules have the potential to be administered orally and to successfully traverse the blood/brain barrier. Unfortunately, however, few compounds have been identified thusfar which are promising enough to go to clinical trials (for reviews of this field, see e.g., Thoenen & Sendtner, *Nat. Neurosci.,* 2002, *Supplement* 5:1046-1050; Saragovi & Gehring, *Trends Pharmacol. Sci.,* 2000, 21:93-98; Xie & Longo, *Prog. Brain Res.,* 2000, 128:333-347.

Exemplary small neurotrophic molecules have been disclosed in PCT/US2004/021399, filed Jul. 2, 2004, published as WO2005/006945 on Jan. 27, 2005, and U.S. application Ser. No. 11/323,987, filed Dec. 30, 2005, published as USSN 2006/0160812 on Jul. 20, 2006, both of which are incorporated by reference in their entireties and for all purposes.

An abnormal rate of apoptosis may be responsible for at least some of the neuronal cell death in neurodegenerative diseases such as Alzheimer's disease and Parkinson's disease (Thompson, *Science,* 1995, 267:1456-1462). Accordingly, without wishing to be bound by any theory, inhibitors of the apoptosis (and other forms of nerve cell death) pathways therefore can be used to promote neuronal survival. Peptide-based inhibitors of caspases, key enzymes in the apoptosis pathway, will suffer from the same drawback as neurotrophins in terms of their ability to cross the blood-brain barrier. Small molecule inhibitors of the apoptosis pathway are still in the early exploratory stage (for review, see Huang, *Chem. & Biol.,* 2002, 9:1059-1072).

SUMMARY OF THE INVENTION

In accordance with the present invention, there are provided novel compounds that have a variety of properties, i.e., antioxidant, anti-inflammatory, antiviral, antibacterial, and antifungal properties. Invention compounds, therefore, have the ability to impart a variety of beneficial physiological effects, e.g., to protect neurons and/or to promote neuroregeneration and/or to promote memory formation and/or to act as protein phosphatase or kinase inhibitors and/or to act as lipoxygenase inhibitors. Such compounds are useful for treatment of a variety of indications, including neurodegenerative diseases and conditions.

In accordance with another aspect of the present invention, there are provided formulations containing one or more of the compounds described herein, optionally further containing additional neurologically active compound(s) and/or adjuvants to facilitate delivery thereof across the blood/brain barrier.

In still another aspect of the present invention, there are provided methods for treating a wide variety of indications, including neurological indications such as acute neural injuries, chronic injuries, promoting memory formation, and the like.

The multiple panels of FIG. 3 collectively demonstrate that an invention compound, such as J147, facilitates the induction of LTP in Schaffer collateral CA1 pyramidal cell synapses in rat hippocampal slices. Specifically, FIG. 3A demonstrates the effect of J147 (1 μM) on basal synaptic transmission. Hippocampal slices were exposed to J147 during the time indicated by the black bar. The field excitatory postsynaptic potential (fEPSP) slope is expressed as the percentage of the value immediately before the addition of J147.

Figure 3A:
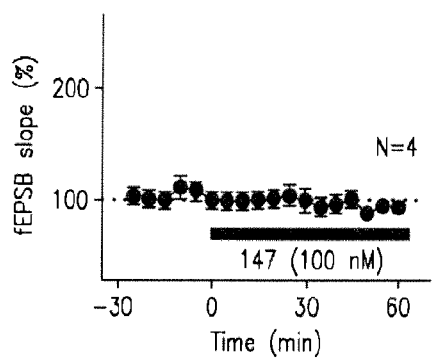
Figure 3B:
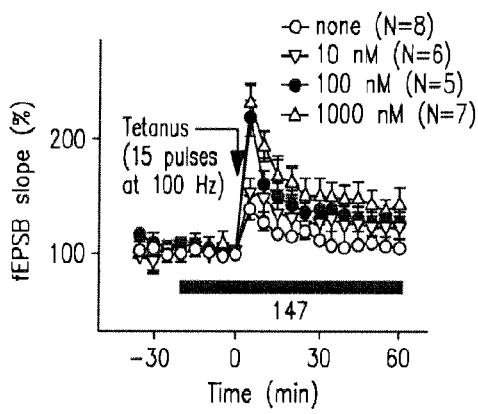
Figure 3C:
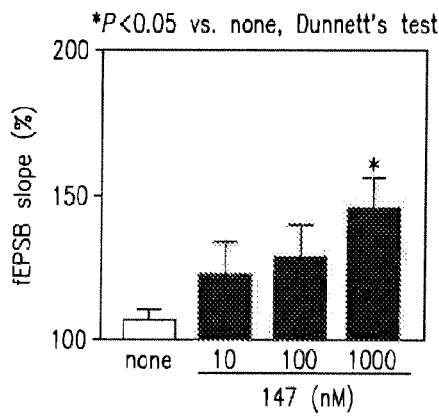

FIGS. 3B and 3C demonstrate that J147 does not affect basal synaptic transmission. Instead, J147 is seen to facilitate the induction of LTP after a weak tetanic stimulation (15 pulses at 100 Hz), which alone does not induce LTP in control slices. The effect of J147 is dose-dependent. The hippocampal slices were untreated or exposed to J147 for the time indicated by the black bar, and weak tetanic stimulation was applied at time 0. The fEPSP slope is expressed as the percentage of the value immediately before the application of weak tetanic stimulation. FIG. 3B illustrates the time course of changes in the fEPSP slope.

Figure 3D:
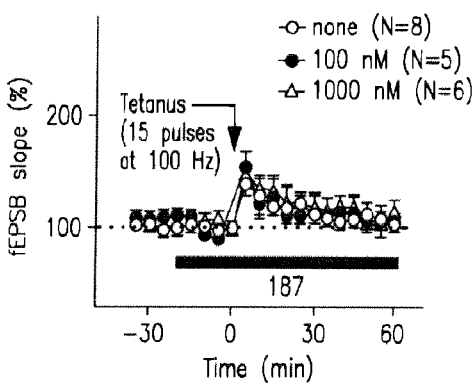

To compare the data among the groups, the averages of the fEPSP slopes 30-60 min after tetanic stimulation were calculated as an index of LTP magnitude; the results are shown in FIG. 3C. All the data are the mean±SEM *P>0.05 vs none. FIG. 3D is a negative control, employing an inactive compound (i.e., the alkene form of J147 in which nitrogens are replaced by carbons).

Figures 4A, 4B:
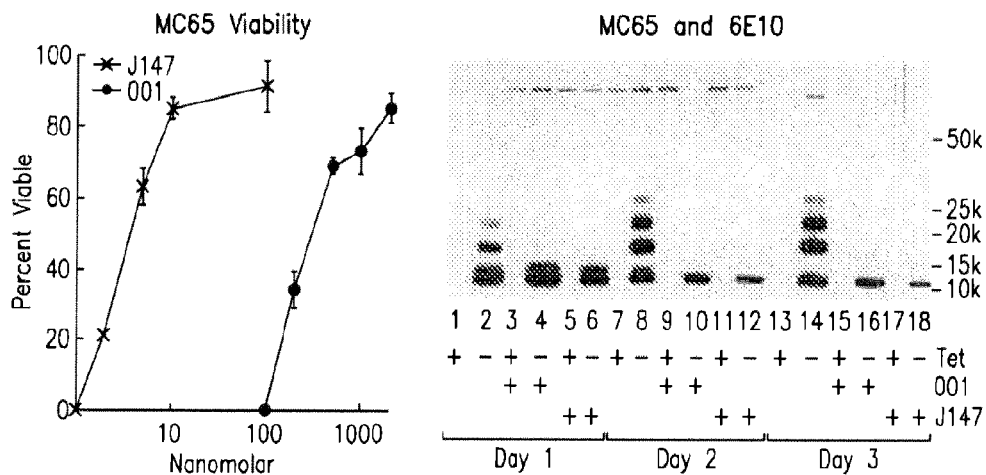

The multiple panels of FIG. 4 demonstrate that J147 and CNB-001 are neuroprotective against intracellular protein aggregation and toxicity. FIG. 4A illustrates the viability of MC-65 cells upon exposure to the indicated concentrations of compounds, and the degree to which synthesis of the C-terminal fragment of APP is induced by the removal of tetracycline. Cell death was determined 5 days later by the MTT assay and confirmed visually. The data are plotted as percent viable, relative to controls of drug plus un-induced cells.

FIG. 4B illustrates the intracellular aggregation of APP C-99 fragments in MC-65 cells, as assayed on days 1, 2 and 3 following tet removal in the presence (+) or absence (−) of 1 μM CNB-001 or 10 nM J147. APP fragments were detected with antibody 6E10.

Figure 5:
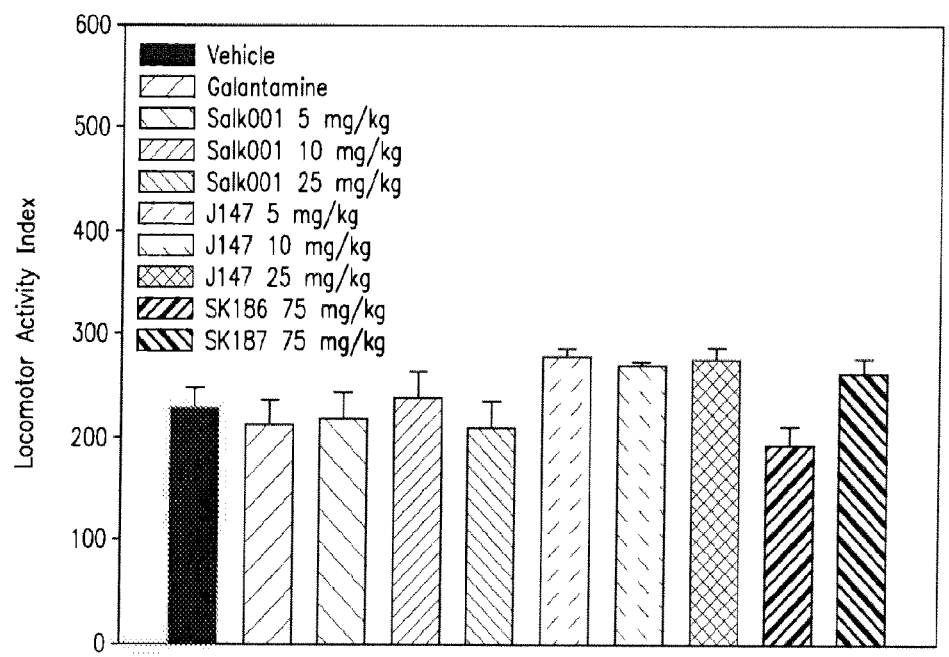

FIG. 5 illustrates the effect of galantamine, compound CNB-001, compound J147, compound SK186 and compound SK187 on exploration of an open field apparatus by adult Wistar rats. Data represent mean±SEM locomotion, measured as the number of lines crossed on the floor of the apparatus in a 5 minute acclimatization period immediately prior to the test period.

Figure 6:
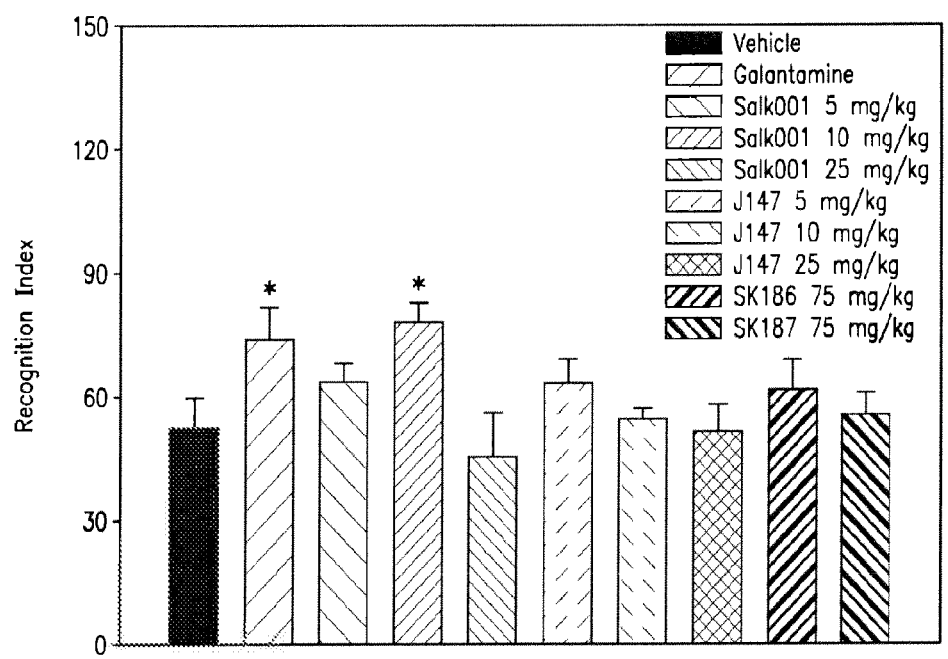

FIG. 6 illustrates the effect of galantamine, compounds CNB-001, J147, SK186 and SKI 87 on object recognition task in Wistar rats. The data represent mean±SEM. *p<0.05 compared with the vehicle control.

Figure 7:
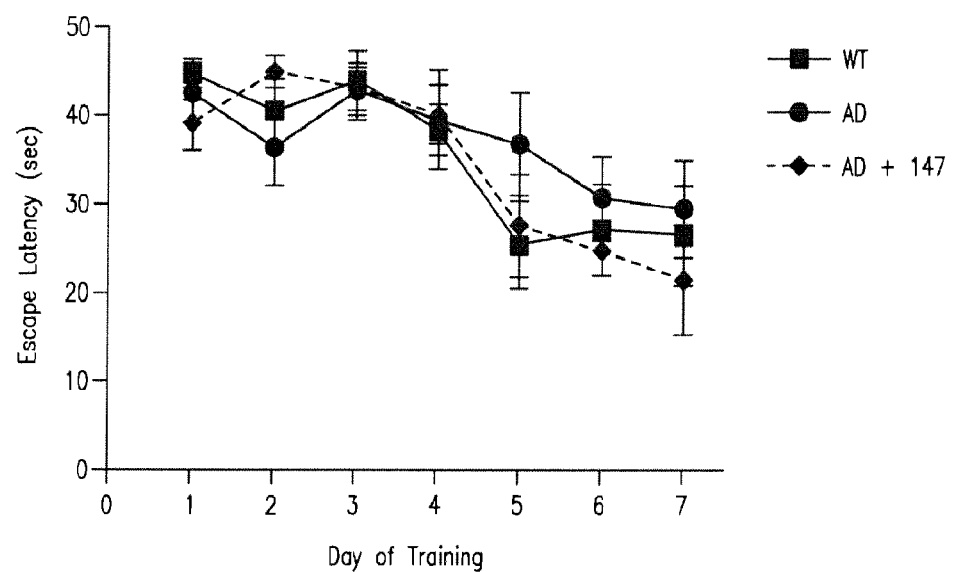

FIG. 7 illustrates that J47 improves spatial learning and memory in the Morris Water Maze. A circular water tank four feet in diameter, containing water at 26-27° C., is made opaque with white pigment, and a platform placed in the NW quadrant. Mice were randomly introduced to the tank facing the wall in one of the other quadrants for a trial of 50 s or until they found the platform. Upon reaching the platform, or at the end of the 50 s, the mice were placed on the platform, the mice were left on the platform for 15 s. There were four trials per mouse each day for seven consecutive days. The data are presented as the average time to reach the platform (escape latency) of the 4 daily trials for each group of mice. There are 3 groups of 5 mice each. One is wild type (circles), another is a double transgenic (mutated PS1 and APP) Alzheimer's mouse model (rectangle), and the third is the AD mouse plus J147 that has been in the food for 4 months at 100 ppm (diamond). The data show that the AD mice have a deficit in memory relative to wild type animals that is corrected by the ingestion of J147.

DETAILED DESCRIPTION OF THE INVENTION

In a first aspect, the present invention provides compounds having the structure of Formula (I):

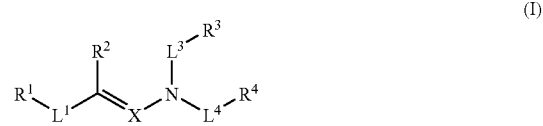

all pharmaceutically acceptable salts, stereoisomers and tautomers thereof,
wherein:
  $R^1$ is selected from the group consisting of optionally substituted aryl and optionally substituted heteroaryl;
  $R^2$ is selected from the group consisting of H, optionally substituted alkyl and optionally substituted alkenyl; or
  $R^2$ is selected from the group consisting of optionally substituted alkylene and optionally substituted alkenylene, such that:
    $R^1$ and $R^2$, together with $L^1$ and the carbon to which $R^2$ is attached, cooperate to form an optionally substituted bicyclic ring, or
    when $R^2$ and $L^3$ are both optionally substituted alkenylene, $R^2$ and $L^3$ cooperate to form an optionally substituted pyrazole ring;
  $R^3$ is selected from the group consisting of optionally substituted alkyl, optionally substituted cycloalkyl, optionally substituted aryl, optionally substituted heteroalkyl, optionally substituted heterocycloalkyl, optionally substituted hetcroaryl, optionally substituted acyl, optionally substituted thioacyl, optionally substituted amino, optionally substituted amido, optionally substituted alkoxy, optionally substituted aryloxy, optionally substituted alkylthio, and optionally substituted arylthio;
  $R^4$ is selected from the group consisting of optionally substituted cycloalkyl, optionally substituted aryl, optionally substituted heterocycloalkyl and optionally substituted heteroaryl;
  X is selected from the group consisting of $CR^5$ and N;
  $R^5$ is selected from the group consisting of H, optionally substituted alkyl and optionally substituted alkenyl; or $R^5$ is selected from the group consisting of optionally substituted alkylene and optionally substituted alkenylene, such that $R^1$ and $R^5$, together with the carbon to which $R^5$ is attached, the carbon to which X is attached, and $L^1$, cooperate to form an optionally substituted bicyclic ring; and $L^1$, $L^3$ and $L^4$ are independently selected from the group consisting of a covalent bond, optionally substituted alkylene, and optionally substituted alkenylene.

"Alkyl" refers to straight or branched chain alkyl radicals having in the range of about 1 up to about 12 carbon atoms (e.g., methyl, ethyl, propyl, butyl, and the like). "Substituted alkyl" refers to alkyl further bearing one or more substituents (e.g., 1, 2, 3, 4, or even 5) as set forth herein. "Optionally substituted alkyl" refers to alkyl or substituted alkyl.

"Cycloalkyl" refers to cyclic ring-containing groups containing in the range of about 3 up to about 12 carbon atoms. "Substituted cycloalkyl" refers to cycloalkyl further bearing one or more substituents (e.g., 1, 2, 3, 4, or even 5) selected from alkyl, substituted alkyl, as well as any of the substituents set forth herein. "Optionally substituted cycloalkyl" refers to cycloalkyl or substituted cycloalkyl.

"Heterocycle," "heterocyclic" and like terms refer to cyclic (i.e., ring-containing) groups containing one or more heteroatoms (e.g., N, O, S, or the like) as part of the ring, and having in the range of 1 up to about 14 carbon atoms. "Substituted heterocyclic" and like terms refer to heterocycle further bearing one or more substituents (e.g., 1, 2, 3, 4, or even 5) as set forth herein. Exemplary heterocyclic moieties include saturated rings, unsaturated rings, and aromatic heteroatom-containing ring systems, e.g., epoxy, tetrahydrofuran, oxazoline, pyrrole, pyridine, furan, and the like. "Optionally substituted heterocycle" and like terms refer to heterocycle or substituted heterocycle.

Reference to "optionally substituted bicyclic ring" refers to a bicyclic ring structure as known in the art, optionally including substitutions as defined herein.

"Alkylene" refers to divalent alkyl, and "substituted alkylene" refers to divalent substituted alkyl. Examples of alkylene include without limitation, ethylene (—$CH_2$—$CH_2$—). "Optionally substituted alkylene" refers to alkylene or substituted alkylene.

"Alkene" refers to straight, branched chain, or cyclic hydrocarbyl groups including from 2 to about 20 carbon atoms having at least one, preferably 1-3, more preferably 1-2, most preferably one, carbon to carbon double bond. "Substituted alkene" refers to alkene substituted at 1 or more, e.g., 1, 2, 3, 4, or even 5 positions, with substitution as described herein. "Optionally substituted alkene" refers to alkene or substituted alkene.

"Alkenylene" refers to divalent alkene. Examples of alkenylene include without limitation, ethenylene (—CH=CH—) and all isomeric forms thereof. "Substituted alkenylene" refers to divalent substituted alkene. "Optionally substituted alkenylene" refers to alkenylene or substituted alkenylene.

"Aryl" refers to aromatic groups having in the range of 6 up to about 14 carbon atoms. "Substituted aryl" refers to aryl radicals further bearing one or more substituents (e.g., 1, 2, 3, 4, or even 5) selected from alkyl, substituted alkyl, cycloalkyl, substituted cycloalkyl, hydroxyl, alkoxy, aryloxy, mercapto, alkylthio, arylthio, carbonyl, aryl, substituted aryl, heterocyclic, substituted heterocyclic, halogen, trifluoromethyl, pentafluoroethyl, cyano, cyanoalkyl, nitro, amino, amido, amidino, carboxyl, carbamate, $SO_2X$, wherein X is H, R, $NH_2$, NHR or $NR_2$, $SO_3Y$, wherein Y is H, $NH_2$, NHR or $NR_2$, or C(O)Z, wherein Z is OH, OR, $NH_2$, NHR or $NR_2$, and the like. "Optionally substituted aryl" refers to aryl or substituted aryl.

"Aralkyl" refers to an alkyl group substituted by an aryl group. "Substituted aralkyl" refers to aralkyl further bearing one or more substituents (e.g., 1, 2, 3, 4, or even 5) selected from alkyl, substituted alkyl, cycloalkyl, substituted cycloalkyl, as well as any of the substituents set forth herein. Thus, aralkyl groups include benzyl, diphenylmethyl, and 1-phenylethyl (—CH($C_6H_5$)($CH_3$)) among others. "Optionally substituted aralkyl" refers to aralkyl or substituted aralkyl.

"Heteroaryl" refers to aromatic groups containing one or more heteroatoms (e.g., N, O, S, or the like) as part of the aromatic ring, typically having in the range of 2 up to about 14 carbon atoms, and "substituted heteroaryl" refers to heteroaryl radicals further bearing one or more substituents (e.g., 1, 2, 3, 4, or even 5) selected from alkyl, substituted alkyl, cycloalkyl, substituted cycloalkyl, as well as any of the substituents set forth above.

"Heteroaralkyl" and "heteroarylalkyl" refer to an alkyl group substituted by one or more heteroaryl groups. "Substituted heteroaralkyl" refers to heteroaralkyl further bearing one or more substituents (e.g., 1, 2, 3, 4, or even 5) selected from alkyl, substituted alkyl, cycloalkyl, substituted cycloalkyl, as well as any of the substituents set forth herein. "Optionally substituted heteroaralkyl" refers to heteroaralkyl or substituted heteroaralkyl.

"Halogen" and "halo" refer to fluorine, chlorine, bromine or iodine.

"Hydroxyl" and "hydroxy" refer to the functionality —OH.

"Alkoxy" denotes the group —OR, where R is alkyl. "Substituted alkoxy" denotes the group —OR, where R is substituted alkyl. "Optionally substituted alkoxy" refers to alkoxy or substituted alkoxy.

"Aryloxy" denotes the group —OR, where R is aryl. "Substituted aryloxy" denotes the group —OR, where R is substituted aryl. "Optionally substituted aryloxy" refers to aryloxy or substituted aryloxy.

"Mercapto" and "thiol" refer to the functionality —SH.

"Alkylthio" and "thioalkoxy" refer to the group —SR, —$S(O)_{n=1-2}$—R, where R is alkyl. "Substituted alkylthio" and "substituted thioalkoxy" refers to the group —SR, —$S(O)_{n=1-2}$—R, where R is substituted alkyl. "Optionally substituted alkylthio" and "optionally substituted thioalkoxy" refers to alkylthio or substituted alkylthio.

"Arylthio" denotes the group —SR, where R is aryl. "Substituted arylthio" denotes the group —SR, where R is substituted aryl. "Optionally substituted arylthio" refers to arylthio or substituted arylthio.

"Amino" refers to unsubstituted, monosubstituted and disubstituted amino groups, including the substituent —$NH_2$, "monoalkylamino," which refers to a substituent having structure —NHR, wherein R is alkyl or substituted alkyl, and "dialkylamino," which refers to a substituent of the structure —$NR_2$, wherein each R is independently alkyl or substituted alkyl.

"Amidino" denotes the group —C(=$NR^q$)$NR'R^s$, wherein $R^q$, $R^r$, and $R^s$ are independently hydrogen or optionally substituted alkyl.

Reference to "amide group" embraces substituents of the structure —C(O)—$NR_2$, wherein each R is independently H, alkyl, substituted alkyl, aryl or substituted aryl as set forth above. When each R is H, the substituent is also referred to as "carbamoyl" (i.e., a substituent having the structure —C(O)—$NH_2$). When only one of the R groups is H, the substituent is also referred to as "monoalkylcarbamoyl" (i.e., a substituent having the structure —C(O)—NHR, wherein R is alkyl or substituted alkyl as set forth above) or "arylcarbamoyl" (i.e., a substituent having the structure —C(O)—NH (aryl), wherein aryl is as defined above, including substituted aryl). When neither of the R groups are H, the substituent is also referred to as "di-alkylcarbamoyl" (i.e., a substituent having the structure —C(O)—NR$_2$, wherein each R is independently alkyl or substituted alkyl as set forth above).

Reference to "carbamate" embraces substituents of the structure —O—C(O)—NR$_7$, wherein each R is independently H, alkyl, substituted alkyl, aryl or substituted aryl.

Reference to "ester group" embraces substituents of the structure —O—C(O)—OR, wherein each R is independently alkyl, substituted alkyl, aryl or substituted aryl.

"Acyl" refers to groups having the structure —C(O)R, where R is hydrogen, alkyl, aryl, and the like as defined herein. "Substituted acyl" refers to acyl wherein the substitutent R is substituted as defined herein. "Optionally substituted acyl" refers to acyl and substituted acyl.

"Cyanoalkyl" refers to the group —R—C≡N, wherein R is optionally substituted alkylene.

Moieties of the present invention may be substituted with various atoms as described herein. As used here, "substitution" denotes an atom or group of atoms that has been replaced with another atom or group of atoms (i.e., substituent), and includes all levels of substitution, e.g. mono-, di-, tri-, tetra-, penta-, or even hex-substitution, where such substitution is chemically permissible. Substitutions can occur at any chemically accessible position and on any atom, such as substitution(s) on carbon and any heteroatom, preferably oxygen, nitrogen, or sulfur. For example, substituted moieties include those where one or more bonds to a hydrogen or carbon atom(s) contained therein are replaced by a bond to non-hydrogen and/or non-carbon atom(s). Substitutions can include, but are not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and heteroatoms in other groups as well known in the art.

Specific examples of substituents contemplated by the present invention include, without limitation, halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR, —SR, —OC(O)R, —OC(S)R, —C(O)R, —C(S)R, —C(O)OR, —C(S)OR, —S(O)R, —S(O)$_2$R, —C(O)NHR, —C(S)NHR, —C(O)NRR, —C(S)NRR, —S(O)$_2$NHR, —S(O)$_2$NRR, —C(NH)NHR, —C(NH)NRR, —NHC(O)R, —NHC(S)R, —NRC(O)R, —NRC(S)R, —NHS(O)$_2$R, —NRS(O)$_2$R, —NHC(O)NHR, —NHC(S)NHR, —NRC(O)NH$_2$, —NRC(S)NH$_2$, —NRC(O)NHR, —NRC(S)NHR, —NHC(O)NRR, —NHC(S)NRR, —NRC(O)NRR, —NRC(S)NRR, —NHS(O)$_2$NHR, —NRS(O)$_2$NH$_2$, —NRS(O)$_2$NHR, —NHS(O)$_2$NRR, —NRS(O)$_2$NRR, —NHR, —NRR, where R at each occurrence is independently H, optionally substituted alkyl, optionally substituted aryl, or optionally substituted heteroaryl. Also contemplated is substitution with an optionally substituted hydrocarbyl moiety containing one or more of the following chemical functionalities: —O—, —S—, —NR—, —O—C(O)—, —O—C(O)—O—, —O—C(O)—NR—, —NR—C(O)—, —NR—C(O)—O—, —NR—C(O)—NR—, —S—C(O)—, —S—C(O)—O—, —S—C(O)—NR—, —S(O)—, —S(O)$_2$—, —O—S(O)$_2$—, —O—S(O)$_2$—O, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, or —NR—P(O)R$_2$—, where R at each occurrence is independently H, optionally substituted alkyl, optionally substituted aryl, or optionally substituted heteroaryl.

Compounds contemplated by the present invention include isomers including stereoisomers (e.g., enantiomer and diasteromers), constitutional isomers, tautomers, conformational isomers, and geometric isomers.

Exemplary constitutional isomers include for example without limitation, isomers resulting from different connectivity of functionalities forming the compound, for example, 1-propyl versus 2-propyl substitution, and the like. Constitutional isomers in combination with tautomerization additionally embrace bonding rearrangements involving the migration of double bonds and substituents. For example, tautomerization in combination with a 1-3 pleiotropic hydrogen shift, as shown in Scheme 1, results in constitutional isomerism.

Scheme 1

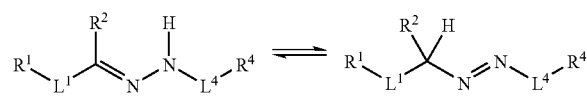

Specifically with respect to the azo compounds produced by tautomerization, also embraced are all pharmaceutically acceptable salts, stereoisomers and any further tautomers thereof, wherein:
R$^1$ is selected from the group consisting of optionally substituted aryl and optionally substituted heteroaryl;
R$^2$ is selected from the group consisting of H, optionally substituted alkyl and optionally substituted alkenyl; or
R$^2$ is selected from the group consisting of optionally substituted alkylene and optionally substituted alkenylene, such that R$^1$ and R$^2$, together with L$^1$ and the carbon to which R$^2$ is attached, cooperate to form an optionally substituted bicyclic ring;
R$^4$ is selected from the group consisting of optionally substituted cycloalkyl, optionally substituted aryl, optionally substituted heterocycloalkyl and optionally substituted heteroaryl; and
L$^1$ and L$^4$ are independently selected from the group consisting of a covalent bond, optionally substituted alkylene, and optionally substituted alkenylene.

Exemplary conformational isomers include for example without limitation, isomers produced by rotation about a bond wherein the rotation is hindered to the extent that separable isomers result, as well known in the art.

Exemplary geometrical isomers include double bonds in e.g., the "E" or "Z" configuration, as well known in the art.

In certain embodiments of the present invention, $R^1$ of compounds of Formula (I) is optionally substituted aryl. Exemplary $R^1$ substituents according to such embodiments include, for example, phenyl, naphthyl, and substituted derivatives thereof. In other embodiments of the present invention, $R^1$ is optionally substituted heteroaryl. Exemplary $R^1$ substituents according to such embodiments include, for example, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, phenyl, isoxazolyl, oxazolyl, and substituted derivatives thereof.

In certain embodiments of the present invention, $R^2$ of compounds of the invention having the structure of Formula (I), is H. In other embodiments of the present invention, $R^2$ is selected from the group consisting of optionally substituted alkyl and optionally substituted alkenyl.

In still other embodiments of the present invention, $R^2$ is selected from the group consisting of optionally substituted alkylene and optionally substituted alkenylene. Accordingly, compounds contemplated by some embodiments of the present invention have the structure of Formula (Ia):

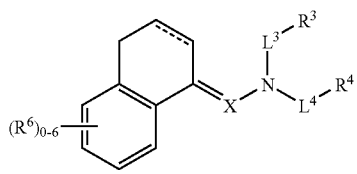

(Ia)

wherein $R^6$ at each occurrence is independently selected from the group consisting of alkyl, substituted alkyl, cycloalkyl, substituted cycloalkyl, hydroxyl, alkoxy, substituted alkoxy, aryloxy, substituted aryloxy, mercapto, alkylthio, arylthio, carbonyl, aryl, substituted aryl, heterocyclic, substituted heterocyclic, halogen, cyano, cyanoalkyl, nitro, amino, amidino, carbamate, $S(O)_n R^7$ and $C(O)R^8$; wherein $R^7$ is H, $R^9$, $NH_2$, $NHR^9$ or $NR^9R^{10}$, wherein $R^8$ is OH, $OR^9$, $NH_2$, $NHR^9$ or $NR^9R^{10}$; $R^9$ and $R^{10}$ at each occurrence are independently optionally substituted alkyl; n=1 or 2; and the symbol "=====" represents either a single bond or a double bond.

In certain embodiments of the present invention, both $R^2$ and $L^3$ are optionally substituted alkenylene, and $R^2$ and $L^3$ cooperate to form an optionally substituted pyrazole ring, as follows:

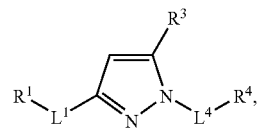

wherein each of $R^1$, $R^3$, $R^4$, $L^1$ and $L^4$ are as previously defined.

In certain embodiments of the present invention, compounds having the generic structure set forth above are further defined as follows:

$R^1$ is optionally substituted aryl;
$R^3$ is optionally substituted alkyl;
$R^4$ is optionally substituted aryl;
X is N; and
$L^1$ and $L^4$ are each a covalent bond.

Exemplary compounds according to this embodiment of the present invention (i.e., compounds wherein $R^2$ and $L^3$ cooperate to form an optionally substituted pyrazole ring) include compounds selected from the group consisting of:

| Compound No. | $R^1$ | $R^3$ | $R^4$ | X | $L^1$ | $L^4$ |
|---|---|---|---|---|---|---|
| A001 | 3-methoxy phenyl | Trifluoro-methyl | 2,4-dimethyl phenyl | N | Covalent bond | Covalent bond |
| A002 | Phenyl | Trifluoro-methyl | Phenyl | N | Covalent bond | Covalent bond |
| A003 | 4-methoxy phenyl | Trifluoro-methyl | Phenyl | N | Covalent bond | Covalent bond |
| A004 | Phenyl | Trifluoro-methyl | 2,4-dimethyl phenyl | N | Covalent bond | Covalent bond |
| A005 | 4-fluoro phenyl | Trifluoro-methyl | Phenyl | N | Covalent bond | Covalent bond |
| A006 | 4-methyl phenyl | Trifluoro-methyl | 4-sulfonylamino phenyl | N | Covalent bond | Covalent bond |
| A007 | 4-sulfonylamino phenyl | Trifluoro-methyl | 3,4-dichloro phenyl | N | Covalent bond | Covalent bond |
| A008 | 4-nitro phenyl | Trifluoro-methyl | Phenyl | N | Covalent bond | Covalent bond |
| A009 | 4-thiomethoxy phenyl | Trifluoro-methyl | 4-fluoro phenyl | N | Covalent bond | Covalent bond |
| A010 | Phenyl | Trifluoro-methyl | 4-amino phenyl | N | Covalent bond | Covalent bond |
| A011 | 4-nitro phenyl | Trifluoro-methyl | Phenyl | N | Covalent bond | Covalent bond |
| A012 | 4-methyl phenyl | Trifluoro-methyl | phenyl | N | Covalent bond | Covalent bond |

In certain embodiments of the present invention, X=CR⁵, thereby providing compounds having the structure of Formula (Ib):

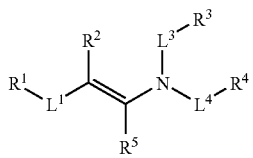

(Ib)

wherein $R^1$, $R^2$, $R^3$, $R^4$, $R^5$, $L^1$, $L^3$ and $L^4$ are as defined for Formula (I). In certain embodiments, $R^3$ is selected from the group consisting of optionally substituted alkyl and optionally substituted acyl. In some embodiments, $R^4$ is optionally substituted aryl. In some embodiments, $R^5$ is H.

In certain embodiments of the invention, $R^5$ of compounds having the structure of Formula (Ib) is selected from the group consisting of optionally substituted alkyl and optionally substituted alkenyl. In other embodiments of the present invention, $R^5$ is selected from the group consisting of optionally substituted alkylene and optionally substituted alkenylene.

In some embodiments, compounds contemplated by the present invention have the structure of Formula (Ic):

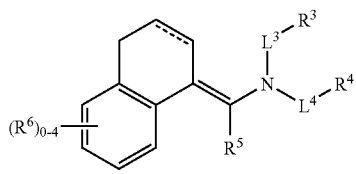

(Ic)

wherein $R^6$ at each occurrence is independently selected from the group consisting of alkyl, substituted alkyl, cycloalkyl, substituted cycloalkyl, hydroxyl, alkoxy, substituted alkoxy, aryloxy, substituted aryloxy, mercapto, alkylthio, arylthio, carbonyl, aryl, substituted aryl, heterocyclic, substituted heterocyclic, halogen, cyano, cyanoalkyl, nitro, amino, amidino, carboxyl, carbamate, $S(O)_nR^7$ and $C(O)R^8$; wherein $R^7$ is H, $R^9$, $NH_2$, $NHR^9$ or $NR^9R^{10}$, wherein $R^8$ is OH, $OR^9$, $NH_2$, $NHR^9$ or $NR^9R^{10}$; $R^9$ and $R^{10}$ at each occurrence are independently optionally substituted alkyl; n=1 or 2; and the symbol ===== represents either a single bond or a double bond.

In some embodiments of the present invention, X=CR⁵, and $R^5$ is optionally substituted alkylene or optionally substituted alkenylene, thereby providing compounds having the structure of Formula (Id):

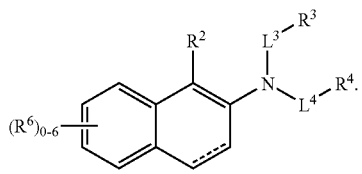

(Id)

wherein $R^6$ at each occurrence is independently selected from the group consisting of alkyl, substituted alkyl, cycloalkyl, substituted cycloalkyl, hydroxyl, alkoxy, substituted alkoxy, aryloxy, substituted aryloxy, mercapto, alkylthio, arylthio, carbonyl, aryl, substituted aryl, heterocyclic, substituted heterocyclic, halogen, cyano, cyanoalkyl, nitro, amino, amidino, carboxyl, carbamate, $S(O)_nR^7$ and $C(O)R^8$; wherein $R^7$ is H, $R^9$, $NH_2$, $NHR^9$ or $NR^9R^{10}$, wherein $R^8$ is OH, $OR^9$, $NH_2$, $NHR^9$ or $NR^9R^{10}$; $R^9$ and $R^{10}$ at each occurrence are independently optionally substituted alkyl; n=1 or 2; and the symbol ===== represents either a single bond or a double bond.

In certain embodiments of the present invention, X of compounds of Formula (I) is nitrogen, thereby providing compounds having the structure of Formula (Ie):

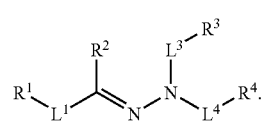

(Ie)

In certain embodiments of the present invention, $L^1$ and $R^1$ of compounds having the structure of Formula (Ie) can be further defined so as to produce compounds of the present invention having the structure of Formula (If):

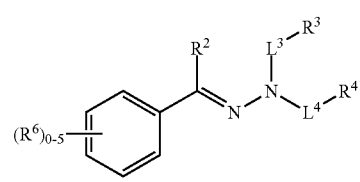

(If)

wherein $R^6$ at each occurrence is independently selected from the group consisting of alkyl, substituted alkyl, cycloalkyl, substituted cycloalkyl, hydroxyl, alkoxy, substituted alkoxy, aryloxy, substituted aryloxy, mercapto, alkylthio, arylthio, carbonyl, aryl, substituted aryl, heterocyclic, substituted heterocyclic, halogen, cyano, cyanoalkyl, nitro, amino, amidino, carboxyl, carbamate, $S(O)_nR^7$ and $C(O)R^8$; wherein $R^7$ is H, $R^9$, $NH_2$, $NHR^9$ or $NR^9R^{10}$, wherein $R^8$ is OH, $OR^9$, $NH_2$, $NHR^9$ or $NR^9R^{10}$; $R^9$ and $R^{10}$ at each occurrence are independently optionally substituted alkyl; and n=1 or 2.

In certain embodiments of the present invention, compounds having the structure of Formula (Ig) are contemplated:

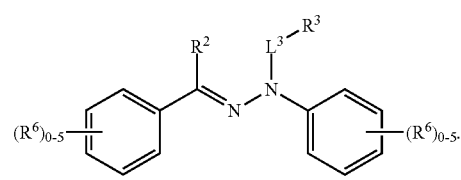

(Ig)

In certain embodiments of the present invention, $R^2$ of compounds of the invention having the structure of Formula (Ig) is H. In certain embodiments, a presently preferred compound of the present invention is referred to as compound J147, having the following structure:

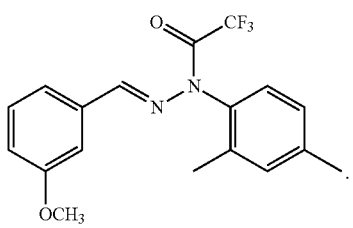

(J147)

In certain embodiments of the present invention, $L^3$ of compounds of the invention having the structure of Formula (Ic) is methylene. In certain embodiments, $L^4$ of compounds of the invention having the structure of Formula (Ie) is methylene. In certain embodiments, $L^3$ of compounds of the invention having the structure of Formula (Ie) is ethylene. In certain embodiments, $L^4$ of compounds of the invention having the structure of Formula (Ie) is ethylene. In certain embodiments, $L^3$ of compounds of the invention having the structure of Formula (Ie) is ethenylene. In certain embodiments, $L^4$ of compounds of the invention having the structure of Formula (Ie) is ethenylene.

As recognized by those of skill in the art, invention compounds can be readily prepared employing standard synthetic methods. For example, curcumin can be condensed with phenyl hydrazine by warming to reflux overnight in toluene. Optionally, a catalytic amount of acid (HCl) can be employed. Preferably, pure curcumin (vs. technical grade) and freshly distilled phenyl hydrazine will be employed.

As another example, 3-methoxy benzaldehyde can be condensed with 2,4-dimethylphenyl hydrazine in methanol employing standard hydrazone preparation conditions (e.g., heating in the microwave to speed the reaction time). Next, the free NH is acylated with TFAA (trifluoroacetic anhydride) plus catalytic (0.1%) amounts of DMAP (dimethylamino pyridine), THF (tetrahydrofuran) or DCM (dichloromethane).

As yet another example, pyrazoles contemplated by the present invention can be prepared by reaction of a suitably substituted 1,3-dione with a suitably substituted hydrazine (e.g., phenylhydrazine). See, for example, J. Med. Chem. 40:3057-63 (1997).

Invention compounds can optionally be employed in the form of a composition which includes a compound having the structure of Formula (I) and a pharmaceutically acceptable carrier therefor. In some embodiments, the pharmaceutically acceptable carrier is suitable for oral administration.

In some embodiments, invention compounds can optionally be employed in the form of pharmaceutically acceptable salts. "Pharmaceutically acceptable" refers to properties of a compound, including safety, toxicity, and the like, such that a reasonably prudent medical or veterinary practitioner would not be dissuaded from administration of such compound to a subject. Such salts are generally prepared by reacting invention compounds with a suitable organic or inorganic acid or base. Representative organic salts include methanesulfonate, acetate, oxalate, adipate, alginate, aspartate, valerate, oleate, laurate, borate, benzoate, lactate, phosphate, toluenesulfonate (tosylate), citrate, malate, maleate, fumarate, succinate, tartrate, napsylate, methanesulfonate, 2-naphthalenesulfonate, nicotinate, benzenesulfonate, butyrate, camphorate, camphorsulfonate, cyclopentanepropionate, digluconate, dodecylsulfate, glucoheptanoate, glycerophosphate, heptanoate, hexanoate, undecanoate, 2-hydroxyethanesulfonate, ethanesulfonate, and the like. Representative inorganic salts can be formed from inorganic acids such as sulfate, bisulfate, hemisulfate, hydrochloride, chlorate, perchlorate, hydrobromide, hydroiodide, and the like. Examples of a base salt include ammonium salts; alkali metal salts such as sodium salts, potassium salts, and the like; alkaline earth metal salts such as calcium salts, magnesium salts, and the like; salts with organic bases such as dicyclohexylamine salts, N-methyl-D-glucamine, phenylethylamine, and the like; and salts with amino acids such as arginine, lysine, and the like. Such salts can readily be prepared employing methods well known in the art.

In accordance with another embodiment of the present invention, there are provided formulations comprising one or more of the above-described compounds and a pharmaceutically acceptable carrier therefor. Exemplary pharmaceutically acceptable carriers include solids, solutions, emulsions, dispersions, micelles, liposomes, and the like. Optionally, the pharmaceutically acceptable carrier employed herein further comprises an enteric coating.

Pharmaceutically acceptable carriers contemplated for use in the practice of the present invention are those which render invention compounds amenable to oral delivery, sublingual delivery, transdermal delivery, subcutaneous delivery, intracutaneous delivery, intrathecal delivery, intraocular delivery, rectal delivery, intravenous delivery, intramuscular delivery, topical delivery, nasal delivery, intraperitoneal delivery, vaginal delivery, intracranial delivery, intraventricular delivery, and the like.

Thus, formulations of the present invention can be used in the form of a solid, a solution, an emulsion, a dispersion, a micelle, a liposome, and the like, wherein the resulting formulation contains one or more of the compounds of the present invention, as an active ingredient, in admixture with an organic or inorganic carrier or excipient suitable for enterable or parenteral applications. The active ingredient may be compounded, for example, with the usual non-toxic, pharmaceutically acceptable carriers for tablets, pellets, capsules, suppositories, solutions, emulsions, suspensions and any other suitable for use. The carriers which can be used include glucose, lactose, gum acacia, gelatin, manitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening, and coloring agents and perfumes may be used. The active compound(s) is (are) included in the formulation in an amount sufficient to produce the desired effect upon the process or disease condition.

Invention formulations containing the active ingredient may be in a form suitable for oral use, for example, as tablets, troches, lozenges, aqueous or oily suspensions, dispersible powders or granules, emulsions, hard or soft capsules, or syrups or elixirs. Formulations intended for oral use may be prepared according to any method known to the art for the manufacture of pharmaceutical compositions and such formulations may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients used may be, for example (1) inert diluents such as calcium carbonate, lactose, calcium phosphate or sodium phosphate; (2) granulating and disintegrating agents such corn starch, potato starch or alginic acid; (3) binding agents such as gum tragacanth, corn starch, gelatin or acacia, and (4)

lubricating agents such as magnesium stearate, steric acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by such techniques as those described in U.S. Pat. Nos. 4,256,108; 4,160,452; and 4,265,874, to form osmotic therapeutic tablets for controlled release.

In some embodiments, formulations contemplated for oral use may be in the form of hard gelatin capsules wherein the active ingredient is mixed with inert solid diluent(s), for example, calcium carbonate, calcium phosphate or kaolin. They may also be in the form of soft gelatin capsules wherein the active ingredient is mixed with water or an oil medium, for example, peanut oil, liquid paraffin, or olive oil.

Invention formulations may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids, naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention formulations may also be administered in the form of suppositories for rectal administration of the drug. These formulations may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug. Since individual subjects may present a wide variation in severity of symptoms and each drug has its unique therapeutic characteristics, the precise mode of administration, dosage employed and treatment protocol for each subject is left to the discretion of the practitioner.

The term "effective amount" as applied to invention compounds, means the quantity necessary to effect the desired therapeutic result, for example, a level effective to treat, cure, or alleviate the symptoms of a disease state for which the therapeutic compound is being administered, or to establish homeostasis. Amounts effective for the particular therapeutic goal sought will, of course, depend upon a variety of factors including the disorder being treated, the severity of the disorder, the activity of the specific compound used, the route of administration, the rate of clearance of the specific compound, the duration of treatment, the drugs used in combination or coincident with the specific compound, the age, body weight, sex, diet and general health of the patient, and like factors well known in the medical arts and sciences. These and other general considerations taken into account in determining the "effective amount" are known to those of skill in the art and are described, e.g., in Gilman et al., eds., *Goodman And Gilman's: The Pharmacological Bases of Therapeutics*, 8th ed., Pergamon Press, 1990; and *Remington's Pharmaceutical Sciences*, 17th ed., Mack Publishing Co., Easton, Pa., 1990, each of which is herein incorporated by reference. Effective amounts of invention compounds typically fall in the range of about 0.001 up to 100 mg/kg/day; with levels in the range of about 0.05 up to 10 mg/kg/day being preferred.

In accordance with yet another embodiment of the present invention, there are provided methods for treating a wide variety of indications, e.g., neurological conditions, cancer, diabetes, arthritis, Alzheimer's disease, trauma and other acute and/or chronic maladies. Exemplary neurological indications include any disease or condition where promoting memory formation, reducing memory loss, ameliorating memory loss, inhibiting cell death, or the like, is desirable, as well as any disease that is etiologically linked to impaired regulation of neurotrophins or their receptors, inhibition of Bcl-2 or Bcl-$X_L$; inhibition of pro-apoptotic Bcl-2 family members (e.g., Bax and Bad) to prevent unwanted cell death, inhibition of IAP (inhibitor of apoptosis proteins), promotion of IAP binding to caspases, destabilization/blocking of abnormal folding of usually soluble proteins into insoluble, tightly packed shapes, and the like. As used herein, "disease condition" refers to a disorder such as Alzheimer's disease, Parkinson's disease, Huntington's disease, systemic senile amyloidosis, prion disease, scrapic, bovine spongiform encephalopathy, Creutzfeldt-Jakob disease, Gerstmann-Straussler-Scheinker syndrome, type II diabetes, adult onset diabetes, insulinoma, amyotropic lateral sclerosis, amyloid A amyloidosis, AL amyloidosis, familial amyloid polyneuropathy (Portuguese, Japanese and Swedish types), familial transthyretin amyloidosis, familial Mediterranean Fever, familial amyloid nephropathy with urticaria and deafness (Muckle-Wells syndrome), hereditary non-neuropathic systemic amyloidosis (familial amyloid polyneuropathy III), familial amyloidosis of Finnish type, familial amyloid cardiomyopathy (Danish type), isolated cardiac amyloid, isolated atrial amyloidosis, idiopathic (primary) amyloidosis, myeloma or macroglobulinemia-associated amyloidosis, primary localized cutaneous nodular amyloidosis associated with Sjogren's syndrome, reactive (secondary) amyloidosis, hereditary cerebral hemorrhage with amyloidosis of Icelandic type, amyloidosis associated with long term hemodialysis, fibrinogen-associated hereditary renal amyloidosis, amyloidosis associated with medullary carcinoma of the thyroid, lysozyme-associated hereditary systemic amyloidosis, stroke, ischemia (e.g., heart ischemia), trauma, retinal neuropathy, peripheral neuropathy, diabetic neuropathy, background neuropathy, and the like.

Thus, in accordance with a particular embodiment of the present invention, there are provided methods for treating acute neural injury, said method comprising administering an effective amount of a compound as described herein to a subject in need thereof.

As readily recognized by those of skill in the art, acute neural injury embraces such injuries as stroke, spinal cord injury, and the like. In such instances, it is recognized by those of skill in the art that nerve cells die as a result of biochemical pathways which include necrosis and various forms of programmed cell death. In addition, glial cells may participate in the cell death. Without wishing to be bound by any theory, the compounds of the invention are believed to be effective, at least in part, by preventing activation of glial cells, and subsequent release of neurotoxic compounds.

As used herein, "treating" refers to inhibiting or arresting the development of a disease, disorder or condition and/or causing the reduction, remission, or regression of a disease, disorder or condition. Those of skill in the art will understand that various methodologies and assays may be used to assess the development of a disease, disorder or condition, and similarly, various methodologies and assays may be used to assess the reduction, remission or regression of a disease, disorder or condition.

As used herein, "administering" refers to providing a therapeutically effective amount of a compound to a subject, using oral, sublingual, intravenous, subcutaneous, transcutaneous, intramuscular, intracutaneous, intrathecal, epidural, intraocular, intracranial, inhalation, rectal, vaginal, and the like administration. Administration in the form of creams, lotions, tablets, capsules, pellets, dispersible powders, granules, suppositories, syrups, elixirs, lozenges, injectable solutions, sterile aqueous or non-aqueous solutions, suspensions or emulsions, patches, and the like, is also contemplated. The active ingredients may be compounded with non-toxic, pharmaceutically acceptable carriers including, glucose, lactose, gum acacia, gelatin, mannitol, starch paste, magnesium trisilicate, talc, corn starch, keratin, colloidal silica, potato starch, urea, dextrans, and the like.

The preferred route of administration will vary with the clinical indication. Some variation in dosage will necessarily occur depending upon the condition of the patient being treated, and the physician will, in any event, determine the appropriate dose for the individual patient. The effective amount of compound per unit dose depends, among other things, on the body weight, physiology, and chosen inoculation regimen. A unit dose of compound refers to the weight of compound employed per administration event without the weight of carrier (when carrier is used).

Targeted-delivery systems, such as polymer matrices, liposomes, microspheres, nanoparticles, and the like, can increase the effective concentration of a therapeutic agent at the site where the therapeutic agent is needed and decrease undesired effects of the therapeutic agent. With more efficient delivery of a therapeutic agent, systemic concentrations of the agent are reduced because lesser amounts of the therapeutic agent can be administered while accruing the same or better therapeutic results. Methodologies applicable to increased delivery efficiency of therapeutic agents typically focus on attaching a targeting moiety to the therapeutic agent or to a carrier which is subsequently loaded with a therapeutic agent.

Various drug delivery systems have been designed by using carriers such as proteins, peptides, polysaccharides, synthetic polymers, colloidal particles (i.e., liposomes, vesicles or micelles), microemulsions, microspheres and nanoparticles. These carriers, which contain entrapped pharmaceutically useful agents, are intended to achieve controlled cell-specific or tissue-specific drug release.

The compounds described herein can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The compounds described herein, when in liposome form can contain, in addition to the compounds described herein, stabilizers, preservatives, excipients, and the like. The preferred lipids are the phospholipids and the phosphatidyl cholines (lecithins), both natural and synthetic. Methods to form liposomes are known in the art. (See, e.g., Prescott, Ed., Methods in Cell Biology, Volume XIV, Academic Press, New York, N.Y., (1976), p 33 et seq.).

Several delivery approaches can be used to deliver therapeutic agents to the brain by circumventing the blood-brain barrier. Such approaches utilize intrathecal injections, surgical implants (Ommaya, *Cancer Drug Delivery*, 1: 169-178 (1984) and U.S. Pat. No. 5,222,982), interstitial infusion (Bobo et al., *Proc. Natl. Acad. Sci. U.S.A.*, 91: 2076-2080 (1994)), and the like. These strategies deliver an agent to the CNS by direct administration into the cerebrospinal fluid (CSF) or into the brain parenchyma (ECF).

Drug delivery to the central nervous system through the cerebrospinal fluid is achieved, for example, by means of a subdurally implantable device named after its inventor the "Ommaya reservoir". The drug is injected into the device and subsequently released into the cerebrospinal fluid surrounding the brain. It can be directed toward specific areas of exposed brain tissue which then adsorb the drug. This adsorption is limited since the drug does not travel freely. A modified device, whereby the reservoir is implanted in the abdominal cavity and the injected drug is transported by cerebrospinal fluid (taken from and returned to the spine) to the ventricular space of the brain, is used for agent administration. Through omega-3 derivatization, site-specific biomolecular complexes can overcome the limited adsorption and movement of therapeutic agents through brain tissue.

Another strategy to improve agent delivery to the CNS is by increasing the agent absorption (adsorption and transport) through the blood-brain barrier and the uptake of therapeutic agent by the cells (Broadwell, *Acta Neuropathol.*, 79: 117-128 (1989); Pardridge et al., *J. Pharmacol. Experim. Therapeutics*, 255: 893-899 (1990); Banks et al., *Progress in Brain Research*, 91:139-148 (1992); Pardridge, *Fuel Homeostasis and the Nervous System*, ed.: Vranic et al., Plenum Press, New York, 43-53 (1991)). The passage of agents through the blood-brain barrier to the brain can be enhanced by improving either the permeability of the agent itself or by altering the characteristics of the blood-brain barrier. Thus, the passage of the agent can be facilitated by increasing its lipid solubility through chemical modification, and/or by its coupling to a cationic carrier, or by its covalent coupling to a peptide vector capable of transporting the agent through the blood-brain barrier. Peptide transport vectors are also known as blood-brain barrier permeabilizer compounds (U.S. Pat. No. 5,268,164). Site specific macromolecules with lipophilic characteristics useful for delivery to the brain are described in U.S. Pat. No. 6,005,004.

Other examples (U.S. Pat. No. 4,701,521, and U.S. Pat. No. 4,847,240) describe a method of covalently bonding an agent to a cationic macromolecular carrier which enters into the cells at relatively higher rates. These patents teach enhancement in cellular uptake of bio-molecules into the cells when covalently bonded to cationic resins.

U.S. Pat. No. 4,046,722 discloses anti-cancer drugs covalently bonded to cationic polymers for the purpose of directing them to cells bearing specific antigens. The polymeric carriers have molecular weights of about 5,000 to 500,000. Such polymeric carriers can be employed to deliver compounds described herein in a targeted manner.

Further work involving covalent bonding of an agent to a cationic polymer through an acid-sensitive intermediate (also known as a spacer) molecule, is described in U.S. Pat. No. 4,631,190 and U.S. Pat. No. 5,144,011. Various spacer molecules, such as cis-aconitic acid, are covalently linked to the agent and to the polymeric carrier. They control the release of the agent from the macromolecular carrier when subjected to a mild increase in acidity, such as probably occurs within a lysosome of the cell. The drug can be selectively hydrolyzed from the molecular conjugate and released in the cell in its unmodified and active form. Molecular conjugates are transported to lysosomes, where they are metabolized under the action of lysosomal enzymes at a substantially more acidic pH than other compartments or fluids within a cell or body. The pH of a lysosome is shown to be about 4.8, while during the initial stage of the conjugate digestion, the pH is possibly as low as 3.8.

In accordance with still another embodiment of the present invention, there are provided methods for treating chronic neurodegenerative disease, said method comprising administering an effective amount of a compound as described herein to a subject in need thereof.

As readily recognized by those of skill in the art, chronic neurodegenerative disease embraces such indications as Alzheimer's disease, Parkinson's disease, Huntington's disease, amyotrophic lateral sclerosis, glaucoma, retinal degeneration, macular degeneration, age-related hearing loss, mild cognitive impairment, dementia (including, for example, frontotemporal dementia, AIDS dementia, and the like), progressive supranuclear palsy, spinoccrebellar ataxias, and the like.

In accordance with a further embodiment of the present invention, there are provided methods of protecting neurons in a subject in need thereof, said method comprising administering an effective amount of a compound as described herein to said subject. As used herein, the phrase "protecting neurons" refers to preventing nerve damage, deterioration of neurons, and/or death of neurons, no matter what the cause or causative agent. Throughout neuronal life, neurons are subjected to various factors that affect and contribute to the natural aging process, which may result in deterioration of neuronal physiology, morphology, and the like. Neurons are also subject to various factors that cause injury and damage, resulting in reduction or loss of some or all physiological and morphological characteristics. Factors can be endogenous (e.g., cytokines, excitotoxins, and the like; or released following stroke or other injury) or exogenous factors such as alcohol, pharmaceutical agents, and the like.

In accordance with a still further embodiment of the present invention, there are provided methods for promoting neuroregeneration in a subject in need thereof, said method comprising administering an effective amount of a compound as described herein to said subject. As used herein, "neuroregeneration" refers to regrowth of neuron projections to repair damage thereto (where the cell body remains intact) and the sprouting of new projections. Neuroregeneration may be needed in a subject when neuropathies are present. Exemplary neuropathies include retinal neuropathy, peripheral neuropathy, background neuropathy, and the like.

In accordance with yet another embodiment of the present invention, there are provided methods for promoting memory formation, said method comprising administering an effective amount of a compound as described herein to a subject in need thereof.

The invention will now be described in greater detail by reference to the following non-limiting examples. Compounds of the invention, and compounds useful for comparison of neurochemical properties therewith, include the following:

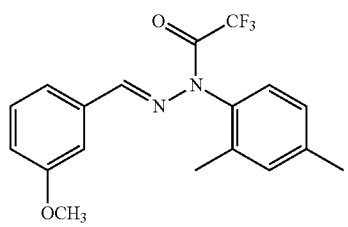

J147

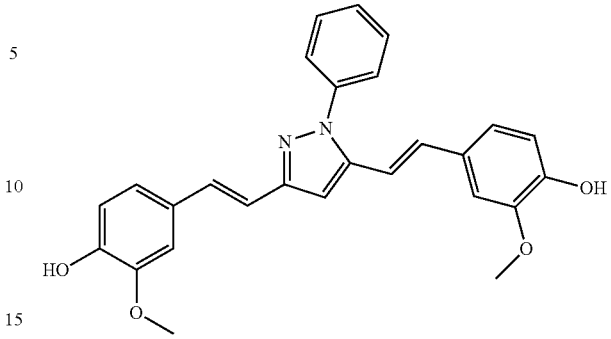

CNB-001

EXAMPLE 1

General Assays for Detecting Neuroprotective Activity

Primary cortical neurons can be prepared from 18-day-old embryos of Sprague-Dawley rats as described (Liu & Schubert, *J. Neurochem.*, 1997, 69:2285-2293 and *J. Neurochem.*, 1998, 71:2322-2329). Briefly, the cerebral cortex is dissected out under an anatomical microscope and is freed of meninges and blood vessels. The cortex is cut into small pieces and is then dissociated by trypsin digestion and passed through a pipette tip. Dissociated neurons are suspended in various media and plated on polylysine-coated 35 mm tissue culture dishes (e.g., $1 \times 10^6$ cells/dish). Several different culture conditions can be used as known in the art. Invention compounds can be added to cell culture dishes. Cell survival can be measured 1-2 days after compound administration.

A serum-containing medium can be used which includes a minimal essential medium (Sigma) containing 30 mM glucose, 2 mM glutamine, 1 mM pyruvate, penicillin (100 U/ml), streptomycin (100 µg/ml), and 10% fetal calf serum. At a plating density of $1 \times 10^6$ cells/dish, most neurons die after one week of culture in this medium. If plated at a density of $2 \times 10^6$ cells/dish, then most neurons survive. The cell density-dependent neuronal survival in this system is most likely dependent on the neurotrophic factors secreted by the neurons, not by the glia. The results are the same when glial proliferation is inhibited by cytosine arabinoside.

A serum-free medium containing DMEM/F-12 plus N2 supplements (Invitrogen) can be employed. When plated at a density of $1 \times 10^6$ cells/dish, almost all neurons die within three days. The cell death mechanisms in this culture medium are most likely to be oxidative stress and trophic factor deficiency.

EXAMPLE 2

Assays for Tropic Factor Withdrawal

The structure-activity relationships of compounds according to the present invention can be determined by measuring trophic factor withdrawal in mouse primary cortical neurons. As shown in FIG. 1A-FIG. 1D, compounds are added to low density primary cultures of E18 rat cortical neurons at the time of plating, and cell survival is determined two days later by a variety of methods.

EXAMPLE 3

Assays for Excitotoxicity

The structure-activity relationships of various compounds according to the present invention can also be determined by measuring excitotoxicity in mouse primary cortical neurons, as follows:

Excitotoxicity assay is carried out with primary cultures of cortical neurons prepared from embryonic day 14 BALB/c mouse embryo cortices as described (Schubert and Piasecki, *J. Neurosci.* 21:7455-7462, 2001). The cells are plated at $1 \times 10^5$ cell/well in 96-well ploy-L-lysine and laminin-coated microtiter plates. Cortical neurons after 11 days of culture are exposed to 10 µM glutamate for 10 min, followed by the addition of varying concentrations of invention compounds. Cell viability is determined 24 hr later with the 3-(4,5-dimethylthiazol-2-yl)-2,5-diphenyltetrazolium bromide (MTT) assay. MTT reduction is a widely used method for measuring cell proliferation and viability (Mosmann, *J. Immunol. Methods* 65:55-63, 1983).

Similar toxicity assays as described above are also conducted with invention compounds using HT22 cells in an assay for oxidative stress. After exposure with 1 mM, 2 mM, 2.5 mM, or 5 mM glutamate, cell viability is determined with the MTT assay.

Compound J147 exhibited an EC50 of ≈5 nM following 5 mM glutamate exposure.

Distinct structure-activity relationships are found with the trophic factor withdrawal and the HT22 assays. Compounds according to the present invention are also found to protect against excitotoxicity in mouse primary cortical neurons with similar efficiencies.

EXAMPLE 4

Pharmacokinetic Evaluation of Invention Compounds

The present example demonstrates the ability of compounds of the invention to cross the blood brain barrier in mice. The pharmacokinetic properties of a single oral dose of exemplary compounds according to the invention, i.e., Cmpd 11-001 and Cmpd J147, are studied in 10-week old female BALB/c mice. Cmpd 11-001 or J147 are emulsified in 2.5% carboxymethyl cellulose at a concentration of 20 mg/ml and administered by gavage at a dosage of 400 mg/kg body weight or 200 mg/kg body weight, respectively. The mice are then sacrificed at various intervals after administration (0, 1 hr, 2 hr, 4 hr, and 6 hr).

Plasma is obtained from blood (mixed with $K_3$EDTA to prevent coagulation) by centrifugation at 4,300 g for 10 min, extracted twice with ethyl acetate/propanol (9:1, v/v). The extracts are centrifuged at 5,000 g for 10 min to form aqueous/organic layers. The organic layer containing Cmpd 11-001 is centrifuged at 20,000 g for 10 min to sediment particles. The extraction recovery from plasma is approximately 90%. Thirty µl thereof were analyzed by HPLC equipped with a C18 reversed phase column—Cmpd 11-001 is detected at 330 nm. The elution solvent system is 50% acetonitrile, 50% water and 1 g/L trifluoroacetic acid with a flow rate of 1 ml/min.

To study the distribution of compounds according to the invention in brain at various time intervals (0, 1 hr, 2 hr, 4 hr, and 6 hr) after gavage (400 mg/kg or 200 mg/kg as noted above), the mice are anesthetized with cloral hydrate and perfused through the heart with phosphate buffered saline (PBS) to remove blood in the brain. The mice are then decapitated, the brains removed, and quickly frozen and stored at −80° C. before further analysis. To measure the level of invention compound in the brain, weighed brain pieces are homogenized by sonication in 3 volumes of PBS. The homogenates are then extracted and measured by HPLC as described above. The results are shown in Table 1 below.

TABLE 1

Plasma concentration and brain content of Cmpd 11-001 or J147 after a single oral dose (400 mg/kg or 200 mg/kg) by gavage

| Time after gavage | Plasma concentration (µg/ml) | | Brain content (µg/g brain) | |
|---|---|---|---|---|
| | 11-001 | J147 | 11-001 | J147 |
| 0 hr | 0 | 0 | 0 | 0 |
| 1 hr | 1.84 | 5.6 | 2.62 | 3.9 |
| 2 hr | 2.30 | 0.3 | 1.28 | 2.8 |
| 4 hr | 1.25 | | 0.89 | |
| 6 hr | 0.67 | | 0.95 | |

This study shows that exemplary compounds according to the invention (11-001 and J147) are rapidly absorbed into blood and are quickly distributed to the brain. The maximum plasma concentration for 11-011 is reached around 2 hr after administration while maximum plasma concentration for J147 is reached even more quickly, only about 1 hr after administration. Maximum brain concentration for both exemplary compounds is reached about 1 hr after gavage, although compound J147 has improved ability to be retained in the brain relative to 11-011, perhaps due to the increased hydrohpobicity of the former. Six hr after administration, the majority of test compound in blood and in brain has been eliminated.

Thus, these results show that exemplary compounds according to the invention can be orally absorbed and traverse the blood-brain barrier.

EXAMPLE 5

Preliminary SAR Analysis of J147 Using the TFW, MC65, and HT-22 Oxytosis Assays

Preliminary SAR analyses were carried out on the series of compounds set forth below, based on the following generic structure:

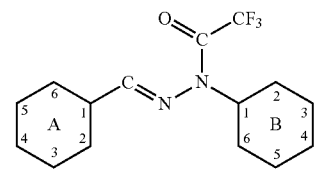

Results are summarized in the following table:

| Compound | A | B | HT-22 $EC_{50}$ | TFW $EC_{50}$ | MC65 $EC_{50}$ |
|---|---|---|---|---|---|
| J147 | 3 $OCH_3$ | 2,4 dimethyl | 6 nM | 50 nM | 10 nM |
| Sk35 | 4 $OCH_3$ | 2,4 dimethyl | 4 nM | 35 nM | 10 nM |
| HF 38FP | H | H | 33 nM | 70 nM | 80 nM |
| HF 39FP | H | 2,4 dimethyl | 37 nM | >1 µM | 220 nM |
| HF 40FP | 3 $OCH_3$ | H | 75 nM | 100 nM | 250 nM |
| HF 41FP | H | 4 methyl | 33 nM | >1 µM | >1 µM |
| HF 42FP | 3 $OCH_3$ | 4 methyl | 80 nM | 700 nM | 50 nM |
| HF 43FP | H | 2 methyl | 50 nM | 800 nM | 400 nM |
| HF 43 FO | 3 $OCH_3$ | 2 methyl | 68 nM | >1 µM | 130 nM |
| Sk36 | 4 $CO_2H$ | 2.4 dimethyl | 100 nM | 300 nM | 300 nM |
| Sk37 | 4 $OCO_2H$ | 2,4 dimethyl | >1 µM | >1 µM | >1 µM |
| J147A | 3 $OCH_3$ TFA replaced with acetyl | 2,4 dimethyl | 70 nM | >1 µM | 280 nM |

HT22 = Oxidative glutamate toxicity (oxytosis)
TFW = Trophic factor withdrawal assay
MC65 = Intracellular amyloid toxicity

EXAMPLE 6

Invention Compounds Alter CREB Phosphorylation

The present example demonstrates the ability of invention compounds to alter activity of a kinase or a phosphatase which is involved in phosphorylation of the neuroprotective transcription factor, cyclic-AMP binding protein (CREB). CREB activation has been linked to cell survival and accordingly, is considered to be a validated therapeutic target (Vaishnov, et al, Biochem. Biophys. Res. Commun. 307:855-860 (2003)). Similar to the concept of programmed cell death which involves transcription factors pivotal in switching on the nerve cell death program is the transcriptional control of programmed cell life. For example, recent studies of the activation of the CREB transcription factor in stroke models have shown that CREB is phosphorylated (and presumably activated) in neurons that survive this insult. Further studies show that the CREB survival pathway may be inactivated by neurotoxins and genes involved in neurodegenerative disorders.

CREB phosphorylation in response to oxidative stress is evaluated in the presence of invention compounds. Glutamate is added to HT22 cells in the presence or absence of Cmpd CNB-001 (at 1 µM). The ratio of phosphorylated CREB to total CREB is then measured as a function of time. Furthermore, all of the HT22 cells die in the absence of Cmpd CNB-001, and over 90% live in the presence of Cmpd CNB-001.

A panel of 14 protein kinases was screened against Cmpd CNB-001. Cmpd CNB-001 partially inhibited the nerve-specific isoform of JNK and JNK-3 kinases. None of the other enzymes that were assayed, including JNK-1 or JNK-2, were affected. In HT22 cells and primary cortical neurons, Cmpd CNB-001 blocked p38 and JNK phosphorylation caused by glutamate by about 30%, and inhibited cell death. The phosphorylation of the other tested kinases was not altered.

EXAMPLE 7

Neuroprotective Effects of Invention Compounds Against Oxidative Stress

The present example demonstrates the protective effects imparted by invention compounds against glutamate induced oxidative stress. See FIG. 1D. See also Tan et al. (Curr. Topics Med. Chem. 1:497-506 (2001)) for further information regarding signaling pathways used to kill and protect HT22 cells from oxidative stress-induced cell death.

HT22 hippocampal neurons are treated with 5 mM glutamate and increasing concentrations of invention compounds. Cell viability is measured 24 hr later by the MTT assay (Davis and Maher, Brain Res. 652:169-173 (1994)).

EXAMPLE 8

Effects of Invention Compounds on Nerve Cells Subjected to Chemical Ischemia Ischemia due to the loss of blood supply can be a problem with diseases affecting brain vascularization. The present example demonstrates the protective effects imparted by invention compounds against chemically induced ischemia.

Most cell culture models of ischemia utilize primary cortical cultures that are exposed to some form of oxygen and glucose deprivation. While these assays may come closer to mimicking the in vivo conditions than assays employing neuronal cell lines, they have a number of problems that make them difficult to use for the routine screening of potential neuroprotective compounds. The most serious problem is that the condition needed to kill a fixed percentage of cells are highly variable from experiment to experiment, making it very difficult to get accurate values for neuroprotective activity. In order to circumvent this and other problems, a mouse nerve cell line was used in combination with chemical ischemia as a screen for potential neuroprotective drugs for ischemia. To induce chemical ischemia, iodoacetic acid (IAA), a well known, irreversible inhibitor of the glycolytic enzyme glyceraldehyde 3-phosphate dehydrogenase (G3PDH) (see B. S. Winkler et al., Modulation of the Pasteur effect in retinal cells: implications for understanding compensatory metabolic mechanisms, in Exp Eye Res 76 (2003) 715-723) was used in combination with the HT22 mouse hippocampal cell line. IAA has been used in a number of other studies to induce ischemia in nerve cells. The changes following IAA treatment of neural cells are very similar to changes which have been seen in animal models of CNS trauma and ischemia. These include alterations in membrane potential, breakdown of phospholipids, loss of ATP, and an increase in reactive oxygen species. A 2 hr treatment of the HT22 cells with 20 µM IAA induces over 90% cell death 20 hr later. This toxic dose is highly reproducible from assay to assay; since only one dose of IAA needs to be used, it makes it quite easy to screen different compounds over a wide range of concentrations.

Figure 1A:
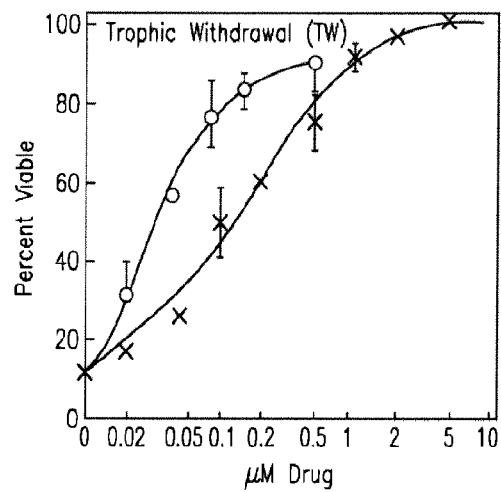
FIG. 1A illustrates the results of a trophic factor withdrawal assay. Primary cortical neurons are prepared from 18-day-old rat embryos, and cultured at low cell density $1 \times 10^6/35$ mm dish, in serum containing medium, with different compounds Viability is then assayed 2 days later using a fluorescent live-dead assay (Molecular Probes).
Figure 1B:
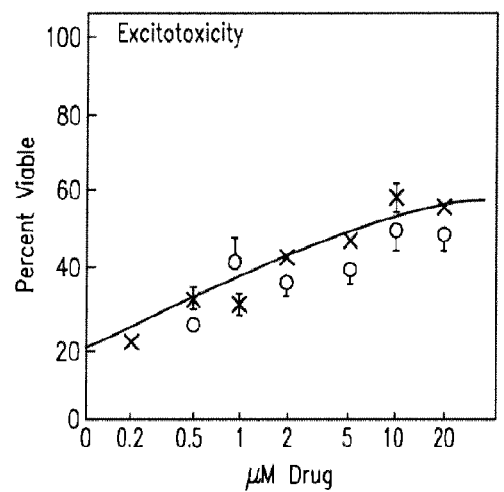
FIG. 1B illustrates the results of an excitotoxicity assay done with E14 mouse primary cultures of cortical neurons, as described previously (D. Schubert & D. Piasecki, *J. Neurosci.* 21 (2001) 7455-7462. After 11 days of culture, cells were exposed to 10 µM glutamate for 10 min, followed by the addition of varying concentrations of lead compounds. Cell viability was determined 24 hr later with the MTT assay and verified using a fluorescent live-dead assay.
Figure 1C:
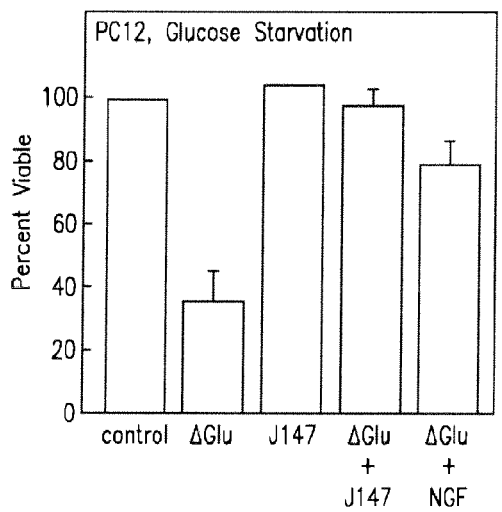
FIG. 1C illustrates the results of a glucose starvation assay. PC12 cells were starved for glucose plus or minus 20 nM J147; cell viability was then determined 48 hr later using the MTT assay (T. Soucek, R. Cumming, R. Dargusch, P. Maher and D. Schubert, *Neuron* 39 (2003) 43-56).
Figure 1D:
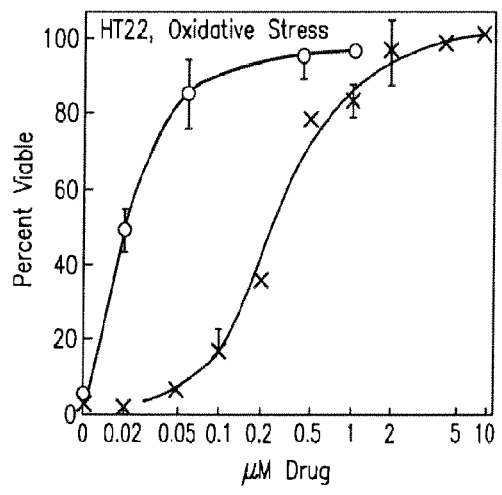
FIG. 1D illustrates the results of an oxidative stress assay. HT22 cells were treated with 5 mM glutamate and different concentrations of two versions of curcumin derivatives. Cell viability was measured 24 hr later by the MTT assay (J. B. Davis and P. Maher, Protein kinase C activation inhibits glutamate-induced cytotoxicity in a neuronal cell line. Brain Res. 652 (1994) 169-173). Legend for FIG. 1A, FIG. 1B and FIG. 1D: x-x, Cmpd CNB-001, o-o, Cmpd J147.
Figure 2:
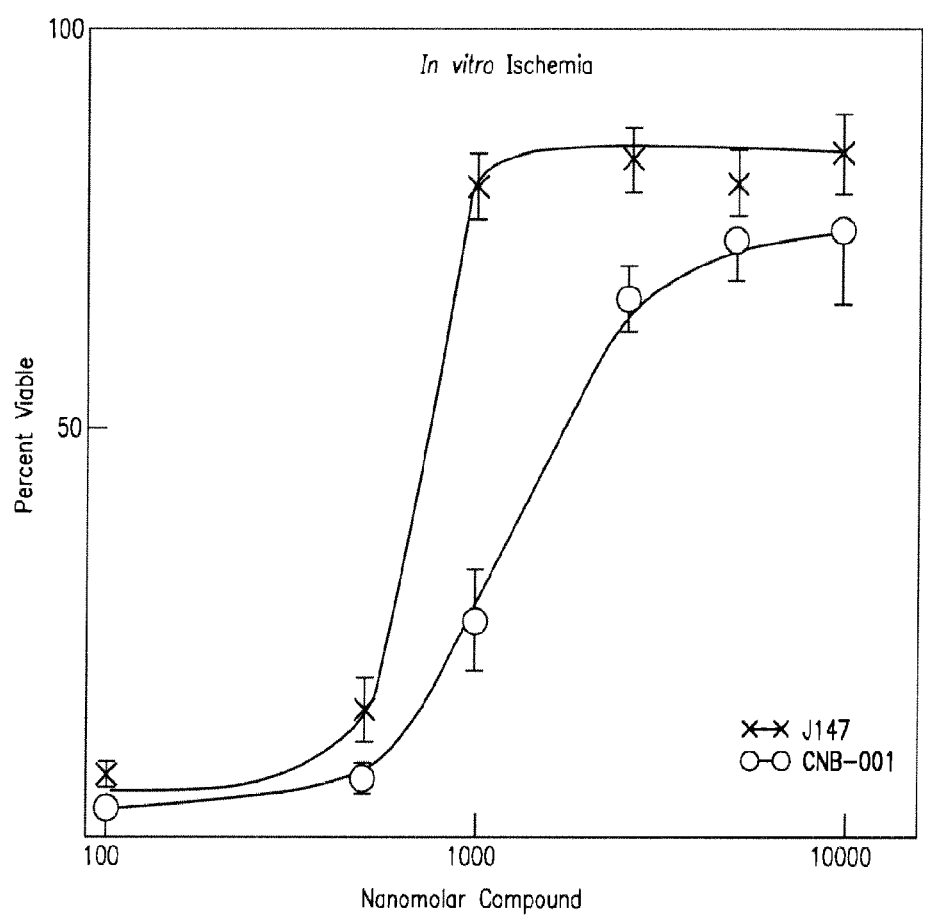
FIG. 2 illustrates the ability of invention compounds CNB-001 and J147 to protect nerve cells from chemical ischemia. HT22 cells were treated with 20 μM iodoacetic acid for 2 hr alone or in the presence of varying concentrations of CNB-001 or J147. % survival was confirmed by microscopy and measured after 24 hr by the MTT assay.

FIG. 2 shows that the cell death caused by treatment of HT22 cells with 20 μM IAA can be prevented by the exemplary compounds of the invention, J147 and the CNB-115 A-related pyrazole CNB-001. Success in this assay has recently been shown to be predictive of the ability to work in the rabbit stroke/ischemia model (see P. Maher et al., A novel approach to screening for new neuroprotective compounds for the treatment of stroke, Brain Res 1173 (2007) 117-125.

EXAMPLE 9

Effects of Invention Compounds on Enzymes Involved in Memory Formation

Invention compounds have the ability to activate CaM Kinase II alpha, a key enzyme involved in memory formation.

To evaluate the ability of a test compound to activate CaM Kinase II alpha, HT22 hippocampal neurons or one week old cortical neurons from embryonic 18 day rats can be prepared according to published procedures (e.g., Soucek et al., Neuron 39:43-56 (2003) and Li et al., Neuron 19:453-463 (1997)). Thus, for example, suitable cells can be treated with 1-2 μM of an exemplary invention compound for a suitable amount of time (e.g., 15, 30, 60 or 120 minutes).

Cells are then lysed and applied to a suitable gel for separation (e.g., P81 phosphocellulose paper, polyacrylamide gel containing SDS, and the like). CaMKII activity can then be assayed using an antibody that recognizes phosphothreonine from both the alpha and beta chains of CaM Kinase II. Invention compounds promote an increase in CaMKII activity of 10% or greater.

EXAMPLE 10

Evaluation of Invention Compounds in Object Discrimination Test with Mice

Sixty young adult, male, C57B1/6 mice from Jackson Laboratories (Bar Harbor, Me.) are used for this study. Mice are received at about 42 days of age. Upon receipt, mice are assigned unique identification numbers (tail marked) and are group housed in polycarbonate cages with filter tops. All animals remain housed in groups of four during the remainder of the study. All mice are acclimated to the colony room for at least two weeks prior to testing and are subsequently tested at an average age of 58 days. During the period of acclimation, mice are examined on a regular basis, handled, and weighed to assure adequate health and suitability. Mice are maintained on a 12/12 light/dark cycle with the light on at 7:30 a.m. The room temperature is maintained between 20 and 23° C. with a relative humidity maintained between 30% and 70%. Chow and water are provided ad libitum for the duration of the study. In each test, animals are randomly assigned across treatment groups and balanced by age. Animals are not disturbed between test days.

All experiments are carried out in ambient temperature under artificial lighting between 9:00 a.m. and 4:00 p.m. Transcribed data are verified item-by-item.

All mice are handled on two consecutive days prior to testing. The mice are then habituated to a circular open field environment (d=18 in, h=15 cm) for one hour in cage groups of four. Each Arena is constructed out of clear acrylic (black construction paper was mounted on sides to block reflection). The presence of reflection lowered subject exploration time in previous pilot studies. Twenty-four hours following habituation, mice are placed back into the same arena for a training trial and allowed to explore a set of two identical objects placed equidistance apart from both each other and the arena walls. Individual mice are trained for a total of 15 minutes and then placed back into their home cages. Twenty-four hours later, subjects are placed back into the same arena in the presence of both the familiar (previously explored) and a novel object. The spatial positions of the familiar and novel object (i.e. left-right sides) are counterbalanced between subjects. The difference in time spent exploring each object during the test trial is used as an index of object recognition and memory retention. Each animal's test trial is recorded and these tapes are observed and scored after test completion. The first 10 min of each session is scored and object recognition is computed using the formula:

(Time spent with novel object*100)/(Total Time exploring both objects)

Data are analyzed by a one-way analysis of variance (ANOVA) followed by post-hoc comparisons with Fisher Tests when appropriate. An effect is considered significant if $p<0.05$. Data is represented as the mean and standard error to the mean. Outliers that fall above and below two standard deviations away from the mean are removed from the final analysis.

EXAMPLE 11

Evaluation of Invention Compounds in Object Discrimination Test with Rats

This model is based on the greater spontaneous exploration of a novel object, compared with a familiar object, shown by rodents (see Ennaceur and Delacour in Behav. Brain Res. 31:47 (1988)). Male Wister rats are assessed for cognitive ability in a test apparatus comprising an open-field arena placed in a sound-attenuated room under dimmed lighting. Images of the open-field are captured by digital camera, and viewed on a monitor in an adjoining room. Each rat is subjected to the procedure separately and care is taken to remove any olfactory/taste cues by cleaning the arena and test objects with alcohol between trials and rats.

Adult male Wistar rats were employed in all rat studies. Animals were placed in the experimental rooms at postnatal day 80 and assigned unique identification numbers (tail marked). Pairs were housed in polycarbonate cages with filter tops and acclimated for 3 days prior to commencing any studies. Animals were maintained in a 12 hour light/dark cycle with room temperature maintained at 22±2° C. with a relative humidity maintained approximately 50%. Food and water were provided ad libitum.

All animals were examined, handled, and weighed for a further two days prior to initiation of the study to assure adequate health and suitability and to minimize non-specific stress associated with manipulation. Each animal was randomly assigned across the treatment groups and balanced by cage numbers. The novel object recognition experiment was performed during the animal's light cycle phase. Drug treatments were balanced across days and animals were only used once The following compounds were used for this study—Reference compound (Galantamine; 3 mg/kg) was dissolved in 0.9% saline and administered i.p. 1 hour pre-test at a dose volume of 1 ml/kg, and all test compounds were handled in solution, and were kept at −80° C. until use. All compounds were administered orally 60 min prior to training at a volume of 1 ml/kg body weight.

Following a 5-minute habituation period, each rat was placed into the test arena in the presence of two identical objects (plastic shapes). Each rat was placed facing the same direction at the same position in the arena, and the time spent actively exploring the objects during a 5-minute test period (T1) was recorded. The rat was returned to its home cage between tests. After 24 hours, each rat was again placed in the test arena for 5 minutes (T2) in the presence of one of the familiar objects and a novel object, and the time spent exploring both objects was again recorded. The presentation order and position of the objects (left/right) was randomized between rats to prevent bias from order or place preference. A preference index for each object, the ratio of the time spent exploring either the familiar object or the novel object over the total time spent exploring both objects (during retention session T2) was used to measure cognitive function.

During the 5 minute acclimatization period in the apparatus, animals were scored for exploratory behavior. Animals treated with J147 at a dose of 5 mg/kg showed a trend towards higher locomotion when compared to vehicle treated controls (p=0.059). No significant difference in locomotion was observed between any of the other treatment groups (FIG. 5).

Data were analyzed by a one-way analysis of variance (ANOVA) followed by post-hoc comparisons with Fisher Tests when appropriate. An effect was considered significant if $p<0.05$. Data in the following tables are presented as the mean and standard error to the mean.

ANOVA Table for Recognition index

|  | DF | Sum of Squares | Mean Square | F-Value | P-Value | Lambda | Power |
|---|---|---|---|---|---|---|---|
| Treatment | 9 | 7657.481 | 850.831 | 2.407 | .0193 | 21.666 | .894 |
| Residual | 70 | 24740.426 | 353.435 | | | | |

Means Table for Recognition index

|  | Count | Mean | Std. Dev. | Std. Err. |
|---|---|---|---|---|
| *vehicle | 8 | 51.922 | 21.822 | 7.715 |
| Galantamine (3 mg/kg) | 8 | 74.037 | 20.711 | 7.323 |
| J147 5 mg/kg | 8 | 63.053 | 16.828 | 5.950 |
| J147 10 mg/kg | 8 | 54.213 | 7.986 | 2.824 |
| J147 25 mg/kg | 8 | 51.372 | 19.151 | 6.771 |
| Salk001 5 mg/kg | 8 | 63.663 | 11.769 | 4.161 |
| Salk001 10 mg/kg | 8 | 77.964 | 12.904 | 4.562 |
| Salk001 25 mg/kg | 8 | 45.226 | 30.571 | 10.809 |
| SK186 | 8 | 61.507 | 20.945 | 7.405 |
| SK187 | 8 | 55.390 | 15.400 | 5.445 |

ANOVA Table for Locomotor Activity

|  | DF | Sum of Squares | Mean Square | F-Value | P-Value | Lambda | Power |
|---|---|---|---|---|---|---|---|
| Treatment | 9 | 70180.813 | 7797.868 | 2.565 | .0130 | 23.087 | .916 |
| Residual | 70 | 212788.375 | 3039.834 | | | | |

Fisher's PLSD for Recognition index
Effect: Treatment
Significance Level: 5%

|  | Mean Diff. | Crit. Diff. | P-Value | |
|---|---|---|---|---|
| *vehicle, Galantamine (3 mg/kg) | −22.114 | 18.748 | .0215 | S |
| *vehicle, J147 5 mg/kg | −11.130 | 18.748 | .2404 | |
| *vehicle, J147 10 mg/kg | −2.291 | 18.748 | .8082 | |
| *vehicle, J147 25 mg/kg | .550 | 18.748 | .9535 | |
| *vehicle, Salk001 5 mg/kg | −11.741 | 18.748 | .2158 | |
| *vehicle, Salk001 10 mg/kg | −26.042 | 18.748 | .0072 | S |
| *vehicle, Salk001 25 mg/kg | 6.697 | 18.748 | .4786 | |
| *vehicle, SK186 | −9.585 | 18.748 | .3114 | |
| *vehicle, SK187 | −3.467 | 18.748 | .7133 | |
| Galantamine (3 mg/kg), J147 5 mg/kg | 10.984 | 18.748 | .2466 | |
| Galantamine (3 mg/kg), J147 10 mg/kg | 19.824 | 18.748 | .0385 | S |
| Galantamine (3 mg/kg), J147 25 mg/kg | 22.665 | 18.748 | .0185 | S |
| Galantamine (3 mg/kg), Salk001 5 mg/kg | 10.374 | 18.748 | .2736 | |
| Galantamine (3 mg/kg), Salk001 10 mg/kg | −3.927 | 18.748 | .6774 | |
| Galantamine (3 mg/kg), Salk001 25 mg/kg | 28.811 | 18.748 | .0031 | S |
| Galantamine (3 mg/kg), SK186 | 12.530 | 18.748 | .1869 | |
| Galantamine (3 mg/kg), SK187 | 18.647 | 18.748 | .0512 | |
| J147 5 mg/kg, J147 10 mg/kg | 8.840 | 18.748 | .3502 | |
| J147 5 mg/kg, J147 25 mg/kg | 11.681 | 18.748 | .2182 | |
| J147 5 mg/kg, Salk001 5 mg/kg | −.610 | 18.748 | .9484 | |
| J147 5 mg/kg, Salk001 10 mg/kg | −14.911 | 18.748 | .1172 | |
| J147 5 mg/kg, Salk001 25 mg/kg | 17.827 | 18.748 | .0620 | |
| J147 5 mg/kg, SK186 | 1.546 | 18.748 | .8699 | |
| J147 5 mg/kg, SK187 | 7.663 | 18.748 | .4177 | |
| J147 10 mg/kg, J147 25 mg/kg | 2.841 | 18.748 | .7634 | |
| J147 10 mg/kg, Salk001 5 mg/kg | −9.450 | 18.748 | .3182 | |
| J147 10 mg/kg, Salk001 10 mg/kg | −23.751 | 18.748 | .0138 | S |
| J147 10 mg/kg, Salk001 25 mg/kg | 8.987 | 18.748 | .3423 | |
| J147 10 mg/kg, SK186 | −7.294 | 18.748 | .4404 | |
| J147 10 mg/kg, SK187 | −1.177 | 18.748 | .9007 | |
| J147 25 mg/kg, Salk001 5 mg/kg | −12.291 | 18.748 | .1953 | |
| J147 25 mg/kg, Salk001 10 mg/kg | −26.592 | 18.748 | .0061 | S |
| J147 25 mg/kg, Salk001 25 mg/kg | 6.147 | 18.748 | .5153 | |
| J147 25 mg/kg, SK186 | −10.135 | 18.748 | .2847 | |
| J147 25 mg/kg, SK187 | −4.017 | 18.748 | .6704 | |
| Salk001 5 mg/kg, Salk001 10 mg/kg | −14.301 | 18.748 | .1327 | |
| Salk001 5 mg/kg, Salk001 25 mg/kg | 18.438 | 18.748 | .0538 | |
| Salk001 5 mg/kg, SK186 | 2.156 | 18.748 | .8192 | |
| Salk001 5 mg/kg, SK187 | 8.274 | 18.748 | .3818 | |
| Salk001 10 mg/kg, Salk001 25 mg/kg | 32.738 | 18.748 | .0009 | S |
| Salk001 10 mg/kg, SK186 | 16.457 | 18.748 | .0844 | |
| Salk001 10 mg/kg, SK187 | 22.574 | 18.748 | .0190 | S |
| Salk001 25 mg/kg, SK186 | −16.281 | 18.748 | .0877 | |
| Salk001 25 mg/kg, SK187 | −10.164 | 18.748 | .2833 | |
| SK186, SK187 | 6.117 | 18.748 | .5173 | |

Fisher's PLSD for Locomotor Activity
Effect: Treatment
Significance Level: 5%

|  | Mean Diff. | Crit. Diff. | P-Value | |
|---|---|---|---|---|
| *vehicle, Galantamine (3 mg/kg) | 14.250 | 54.981 | .6068 | |
| *vehicle, J147 5 mg/kg | −52.875 | 54.981 | .0592 | |
| *vehicle, J147 10 mg/kg | −43.375 | 54.981 | .1201 | |
| *vehicle, J147 25 mg/kg | −49.750 | 54.981 | .0754 | |
| *vehicle, Salk001 5 mg/kg | 8.375 | 54.981 | .7622 | |
| *vehicle, Salk001 10 mg/kg | −12.625 | 54.981 | .6484 | |
| *vehicle, Salk001 25 mg/kg | 16.750 | 54.981 | .5454 | |
| *vehicle, SK186 | 33.250 | 54.981 | .2318 | |
| *vehicle, SK187 | −35.875 | 54.981 | .1974 | |
| Galantamine (3 mg/kg), J147 5 mg/kg | −67.125 | 54.981 | .0174 | S |
| Galantamine (3 mg/kg), J147 10 mg/kg | −57.625 | 54.981 | .0402 | S |
| Galantamine (3 mg/kg), J147 25 mg/kg | −64.000 | 54.981 | .0232 | S |
| Galantamine (3 mg/kg), Salk001 5 mg/kg | −5.875 | 54.981 | .8319 | |
| Galantamine (3 mg/kg), Salk001 10 mg/kg | −26.875 | 54.981 | .3330 | |
| Galantamine (3 mg/kg), Salk001 25 mg/kg | 2.500 | 54.981 | .9280 | |
| Galantamine (3 mg/kg), SK186 | 19.000 | 54.981 | .4930 | |
| Galantamine (3 mg/kg), SK187 | −50.125 | 54.981 | .0733 | |

-continued

Fisher's PLSD for Locomotor Activity
Effect: Treatment
Significance Level: 5%

| | Mean Diff. | Crit. Diff. | P-Value | |
|---|---|---|---|---|
| J147 5 mg/kg, J147 10 mg/kg | 9.500 | 54.981 | .7314 | |
| J147 5 mg/kg, J147 25 mg/kg | 3.125 | 54.981 | .9101 | |
| J147 5 mg/kg, Salk001 5 mg/kg | 61.250 | 54.981 | .0295 | S |
| J147 5 mg/kg, Salk001 10 mg/kg | 40.250 | 54.981 | .1487 | |
| J147 5 mg/kg, Salk001 25 mg/kg | 69.625 | 54.981 | .0138 | S |
| J147 5 mg/kg, SK186 | 86.125 | 54.981 | .0026 | S |
| J147 5 mg/kg, SK187 | 17.000 | 54.981 | .5395 | |
| J147 10 mg/kg, J147 25 mg/kg | −6.375 | 54.981 | .8178 | |
| J147 10 mg/kg, Salk001 5 mg/kg | 51.750 | 54.981 | .0647 | |
| J147 10 mg/kg, Salk001 10 mg/kg | 30.750 | 54.981 | .2685 | |
| J147 10 mg/kg, Salk001 25 mg/kg | 60.125 | 54.981 | .0325 | S |
| J147 10 mg/kg, SK186 | 76.625 | 54.981 | .0070 | S |
| J147 10 mg/kg, SK187 | 7.500 | 54.981 | .7864 | |
| J147 25 mg/kg, Salk001 5 mg/kg | 58.125 | 54.981 | .0386 | S |
| J147 25 mg/kg, Salk001 10 mg/kg | 37.125 | 54.981 | .1824 | |
| J147 25 mg/kg, Salk001 25 mg/kg | 66.500 | 54.981 | .0185 | S |
| J147 25 mg/kg, SK186 | 83.000 | 54.981 | .0036 | S |
| J147 25 mg/kg, SK187 | 13.875 | 54.981 | .6163 | |
| Salk001 5 mg/kg, Salk001 10 mg/kg | −21.000 | 54.981 | .4488 | |
| Salk001 5 mg/kg, Salk001 25 mg/kg | 8.375 | 54.981 | .7622 | |
| Salk001 5 mg/kg, SK186 | 24.875 | 54.981 | .3700 | |
| Salk001 5 mg/kg, SK187 | −44.250 | 54.981 | .1130 | |
| Salk001 10 mg/kg, Salk001 25 mg/kg | 29.375 | 54.981 | .2903 | |
| Salk001 10 mg/kg, SK186 | 45.875 | 54.981 | .1006 | |
| Salk001 10 mg/kg, SK187 | −23.250 | 54.981 | .4019 | |
| Salk001 25 mg/kg, SK186 | 16.500 | 54.981 | .5514 | |
| Salk001 25 mg/kg, SK187 | −52.625 | 54.981 | .0604 | |
| SK186, SK187 | −69.125 | 54.981 | .0145 | S |

The effects of test compounds on memory index are shown in FIG. 6. One-way analysis of variance showed a significant treatment effect. The reference compounds Galantamine (3 mg/kg) as well as CNB-001 at 10 mg/kg significantly increased the recognition index.

EXAMPLE 12

Exemplary Performance Properties of Invention Compounds

Exemplary performance properties of invention compounds are summarized in Table 2, as follows:

TABLE 2

| ASSAYS: | CNB-001 | J147 |
|---|---|---|
| Cell Culture | | |
| Amyloid Toxicity | | |
| Extracellular | 500 nM | 10 nM |
| Intracellular | 200 nM | 3 nM |
| Amyloid Dissociation | + | − |
| Trophic Factor Withdrawal | 500 nM | 10 nM |
| Glucose Starvation | + | + |
| Oxidative Glutamate Toxicity | 500 nM | 5 nM |
| In Vitro Ischemia | | |
| Cortical Nerve | + | + |
| Retinal Ganglion Cells | + | + |
| Mouse hippocampal cells | + | ND |
| Animal Models | | |
| Rabbit stroke | + | ND |
| Memory | + | + |
| Animal | + | + |
| LTP | + | + |
| CREB | + | + |
| CaMKinase II | + | + |
| SAR data | + | + |
| Toxicology-no apparent effect on animal weight or overall health | 500 ppm food several mo. (mice) | 300 mg/kg gavage 10 d (mice) |
| Mode of Action | possible protein kinase inhibitor | class of target known |

ND = not determined
+ = positive result or enzyme activation

The results summarized in Table 2 demonstrate that exemplary compounds according to the invention, i.e., Cmpd CNB-001 and Cmpd J147, have excellent neuroprotective activity.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

That which is claimed is:

1. A compound having the structure of Formula (Ig):

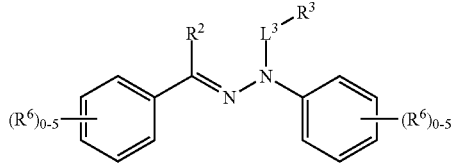

or a pharmaceutically acceptable salt, stereoisomer or tautomer thereof,
wherein:
- $R^2$ is selected from the group consisting of H and methyl;
- $R^3$ is trifluoromethyl or other fluoro substituted alkyl;
- $L^3$ is a carbonyl; and
- $R^6$ at each occurrence is independently selected from the group consisting of alkyl, substituted alkyl, cycloalkyl, substituted cycloalkyl, hydroxyl, alkoxy, substituted alkoxy, aryloxy, substituted aryloxy, mercapto, alkylthio, arylthio, carbonyl, aryl, substituted aryl, halogen, cyano, cyanoalkyl, nitro, amino, amidino, carbamate, $S(O)_nR^7$ and $C(O)R^8$;
- $R^7$ is H, $R^9$, $NH_2$, $HNR^9$ or $NR^9R^{10}$;
- $R^8$ is OH, $OR^9$, $NH_2$, $NHR^9$ or $NR^9R^{10}$;
- $R^9$ and $R^{10}$ at each occurrence are independently optionally substituted alkyl; and n=1 or 2.

2. The compound according to claim 1 having the structure of Formula (1):

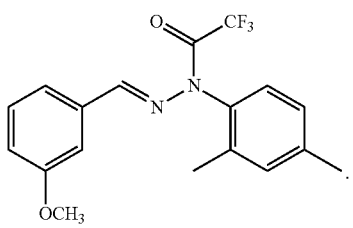

3. A composition comprising a compound according to claim 1 and a pharmaceutically acceptable carrier therefor.

4. A method for treating acute neural injury, treating chronic neurodegenerative disease, protecting neurons in a subject in need thereof, or promoting neuroregeneration and/or memory formation in a subject in need thereof, said method comprising administering an effective amount of a compound according to claim 2 to said subject.

5. The method of claim 4, wherein the chronic neurodegenerative disease is selected from the group consisting of: Alzheimer's disease, Parkinson's disease, Huntington's disease, amytrophical lateral sclerosis, and retinal degeneration.

6. The method of claim 4, wherein the chronic neurodegenerative disease is Alzheimer's disease.

7. A composition comprising a compound according to claim 2 and a pharmaceutically acceptable carrier therefore.

8. The method of claim 4, wherein the acute neural injury is stroke.

9. The compound according to claim 1, wherein $R^6$ at each occurrence is selected from the group consisting of alkyl, substituted alkyl, hydroxyl, alkoxy, substituted alkoxy, halogen, and $C(O)R^8$.

10. The compound according to claim 9, wherein $R^6$ at each occurrence is selected from the group consisting of methyl, methoxy, perfluoromethyl, perfluoromethoxy, hydroxyl, Cl, F, and I.

11. A compound according to claim 1 having the structure of Formula II

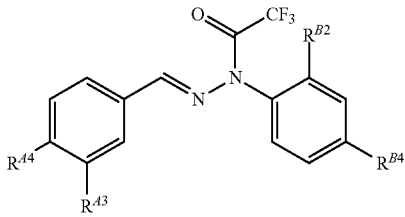

or a pharmaceutically acceptable salt, stereoisomer or tautomer thereof,
wherein:
(i) $R^{A4}$ is H, $R^{A3}$ is methoxy, $R^{B2}$ is methyl, and $R^{B4}$ is methyl; or
(ii) $R^{A4}$ is methoxy, $R^{A3}$ is H, $R^{B2}$ is methyl, and $R^{B4}$ is methyl; or
(iii) $R^{A4}$ is H, $R^{A3}$ is H, $R^{B2}$ is H, and $R^{B4}$ is H; or
(iv) $R^{A4}$ is H, $R^{A3}$ is H, $R^{B2}$ is methyl, and $R^{B4}$ is methyl; or
(v) $R^{A4}$ is H, $R^{A3}$ is methoxy, $R^{B2}$ is H, and $R^{B4}$ is H; or
(vi) $R^{A4}$ is H, $R^{A3}$ is H, $R^{B2}$ is H, and $R^{B4}$ is methyl; or
(vii) $R^{A4}$ is H, $R^{A3}$ is methoxy, $R^{B2}$ is H, and $R^{B4}$ is methyl; or
(viii) $R^{A4}$ is H, $R^{A3}$ is H, $R^{B2}$ is methyl, and $R^{B4}$ is H; or
(ix) $R^{A4}$ is H, $R^{A3}$ is methoxy, $R^{B2}$ is methyl, and $R^{B4}$ is H; or
(x) $R^{A4}$ is COOH, $R^{A3}$ is H, $R^{B2}$ is methyl, and $R^{B4}$ is methyl.

12. A composition comprising a compound according to claim 9 and a pharmaceutically acceptable carrier therefor.

* * * * *